US010912768B2

(12) United States Patent
Rossignol et al.

(10) Patent No.: US 10,912,768 B2
(45) Date of Patent: *Feb. 9, 2021

(54) COMPOUNDS AND METHODS FOR TREATING INFLUENZA

(71) Applicant: Romark Laboratories L.C., Tampa, FL (US)

(72) Inventors: Jean-Francois Rossignol, St. Petersburg, FL (US); J. Edward Semple, Tampa, FL (US)

(73) Assignee: Romark Laboratories L.C., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/448,267

(22) Filed: Jun. 21, 2019

(65) Prior Publication Data

US 2019/0307730 A1 Oct. 10, 2019

Related U.S. Application Data

(63) Continuation of application No. 15/814,949, filed on Nov. 16, 2017, now Pat. No. 10,363,243, which is a continuation of application No. 15/133,534, filed on Apr. 20, 2016, now Pat. No. 9,820,975, which is a continuation of application No. 14/658,409, filed on Mar. 16, 2015, now Pat. No. 9,345,690, which is a continuation of application No. 12/821,571, filed on Jun. 23, 2010, now Pat. No. 9,023,877.

(60) Provisional application No. 61/220,891, filed on Jun. 26, 2009.

(51) Int. Cl.
| | |
|---|---|
| *A61K 31/426* | (2006.01) |
| *A61K 31/454* | (2006.01) |
| *A61K 31/496* | (2006.01) |
| *A61K 31/675* | (2006.01) |
| *A61K 31/7105* | (2006.01) |
| *A61K 45/06* | (2006.01) |
| *H01L 31/12* | (2006.01) |
| *A61K 31/215* | (2006.01) |
| *A61K 31/351* | (2006.01) |
| *A61K 9/00* | (2006.01) |
| *A61K 9/20* | (2006.01) |

(52) U.S. Cl.
CPC .......... *A61K 31/426* (2013.01); *A61K 9/0053* (2013.01); *A61K 9/2086* (2013.01); *A61K 31/215* (2013.01); *A61K 31/351* (2013.01); *A61K 31/454* (2013.01); *A61K 31/496* (2013.01); *A61K 31/675* (2013.01); *A61K 31/7105* (2013.01); *A61K 45/06* (2013.01); *H01L 31/125* (2013.01); *A61K 2300/00* (2013.01)

(58) Field of Classification Search
CPC .................................................. A61K 31/426
See application file for complete search history.

(56) References Cited

U.S. PATENT DOCUMENTS

| | | | |
|---|---|---|---|
| 3,950,351 A | 4/1976 | Rossignol et al. | |
| 4,337,081 A | 6/1982 | Gay | |
| 4,343,945 A | 8/1982 | Gay | |
| 4,416,683 A | 11/1983 | Burow, Jr. | |
| 5,169,846 A | 12/1992 | Crooks | |
| 5,578,621 A | 11/1996 | Rossignol | |
| 6,020,353 A | 2/2000 | Rossignol | |
| 6,117,894 A | 9/2000 | Rossignol | |
| 6,136,835 A | 10/2000 | Camden | |
| 6,849,254 B1 | 2/2005 | Brass et al. | |
| 7,241,781 B2 | 7/2007 | Barrish et al. | |
| 7,285,567 B2 | 10/2007 | Rossignol | |
| 8,124,632 B2 | 2/2012 | Rossignol et al. | |
| 8,541,457 B2 | 9/2013 | Fu et al. | |
| 8,846,727 B2 | 9/2014 | Rossignol et al. | |
| 8,895,752 B2 | 11/2014 | Rossignol et al. | |
| 9,023,877 B2 * | 5/2015 | Rossignol ............ | A61K 31/496 514/370 |
| 9,126,992 B2 | 9/2015 | Rossignol et al. | |
| 9,345,690 B2 * | 5/2016 | Rossignol ............ | A61K 31/215 |
| 9,820,975 B2 * | 11/2017 | Rossignol ............ | H01L 31/125 |
| 10,363,243 B2 * | 7/2019 | Rossignol ............ | A61K 31/454 |
| 2003/0022855 A1 | 1/2003 | Fisher et al. | |
| 2004/0082629 A1 | 4/2004 | Iwataki et al. | |
| 2004/0192746 A1 | 9/2004 | Sanner et al. | |
| 2004/0242518 A1 | 12/2004 | Chen et al. | |
| 2005/0090506 A1 | 4/2005 | Iwataki et al. | |
| 2005/0112751 A1 | 5/2005 | Fang et al. | |
| 2006/0089396 A1 | 4/2006 | Rossignol | |
| 2006/0111409 A1 | 5/2006 | Muto et al. | |

(Continued)

FOREIGN PATENT DOCUMENTS

| | | |
|---|---|---|
| CA | 2618646 A1 | 11/2007 |
| EP | 0 343 894 B1 | 6/1992 |

(Continued)

OTHER PUBLICATIONS

U.S. Appl. No. 15/156,580, filed May 17, 2016, Rossignol et al.
Allen et al., "Identification and Characterization of Mutations in Hepatitis B Virus Resistant to Lamivudine," Hepatology, 1998, 27(6):1670-1677.
Amadi et al., "Effect of nitazoxanide on morbidity and mortality in Zambian children with cryptosporidiosis: a randomized controlled trial," The Lancet, Nov. 2, 2002, 360:1375-1380.
Angus et al., "Resistance fo Adefovir Dipivoxil Therapy Associated With the Selection of a Novel Mutation in the HBV Polymerase," Gastroenterology, 2003, 125:292-297.

(Continued)

*Primary Examiner* — Rei Tsang Shiao
(74) *Attorney, Agent, or Firm* — Foley & Lardner LLP

(57) ABSTRACT

This invention is directed to methods for treating and preventing influenza infection by inhibiting influenza virus HA maturation processes employing compounds of formula I. It is also directed to combinations for treating and preventing influenza infection comprising compounds of formula I and other agents.

10 Claims, 15 Drawing Sheets

(56) References Cited

U.S. PATENT DOCUMENTS

| | | |
|---|---|---|
| 2006/0167053 A1 | 7/2006 | Iino et al. |
| 2006/0194853 A1 | 8/2006 | Rossignol |
| 2007/0004661 A1 | 1/2007 | Stein et al. |
| 2007/0004701 A1 | 1/2007 | Murphy et al. |
| 2007/0015803 A1 | 1/2007 | Rossignol |
| 2007/0110685 A1 | 5/2007 | Auspitz et al. |
| 2007/0167504 A1 | 7/2007 | Rossignol |
| 2008/0097106 A1 | 4/2008 | Rossignol |
| 2008/0161324 A1 | 7/2008 | Johansen et al. |
| 2008/0182837 A1 | 7/2008 | Steurer et al. |
| 2009/0036467 A1 | 2/2009 | Rossignol et al. |
| 2009/0176991 A1 | 7/2009 | Murray et al. |
| 2010/0009970 A1 | 1/2010 | Johansen et al. |
| 2010/0075964 A1 | 3/2010 | Busch et al. |
| 2010/0081713 A1 | 4/2010 | Sharma et al. |
| 2010/0331295 A1 | 12/2010 | Busch et al. |
| 2012/0122939 A1 | 5/2012 | Rossignol et al. |

FOREIGN PATENT DOCUMENTS

| | | |
|---|---|---|
| EP | 1649852 A1 | 4/2006 |
| GB | 1177206 | 1/1970 |
| GB | 2331748 A | 6/1999 |
| JP | S27-122 | 1/1952 |
| JP | 56-158703 A | 12/1981 |
| JP | 64-009978 A | 1/1989 |
| JP | 02-017177 A | 1/1990 |
| JP | 2003-335680 A | 11/2003 |
| SU | 910628 B | 3/1982 |
| WO | WO 95/20567 A1 | 8/1995 |
| WO | WO 95/28393 A1 | 10/1995 |
| WO | WO 98/50035 A1 | 11/1998 |
| WO | WO 00/02851 A1 | 1/2000 |
| WO | WO 00/26202 A2 | 5/2000 |
| WO | WO 02/092584 A1 | 11/2002 |
| WO | WO 03/015774 A1 | 2/2003 |
| WO | WO 03/103648 A1 | 12/2003 |
| WO | WO 2004/028471 A2 | 4/2004 |
| WO | WO 2004/085433 A2 | 10/2004 |
| WO | WO 2006/031291 A2 | 3/2006 |
| WO | WO 2006/042195 A1 | 4/2006 |
| WO | WO 2006/122011 A2 | 11/2006 |
| WO | WO 2007/002559 A1 | 1/2007 |
| WO | WO 2007/008541 A2 | 1/2007 |
| WO | WO 2007/016228 A2 | 2/2007 |
| WO | WO 2007/076034 A2 | 7/2007 |
| WO | WO 2007/125103 A2 | 11/2007 |
| WO | WO 2007/140385 A1 | 12/2007 |
| WO | WO 2008/070707 A1 | 6/2008 |
| WO | WO 2009/001214 A2 | 12/2008 |
| WO | WO 2009/065096 A1 | 5/2009 |
| WO | WO 2009/152356 A2 | 12/2009 |
| WO | WO 2010/026262 A1 | 3/2010 |
| WO | WO 2010/034796 A1 | 4/2010 |
| WO | WO 2010/059606 A2 | 5/2010 |
| WO | WO 2010/107736 A2 | 9/2010 |

OTHER PUBLICATIONS

Balachandran et al., "Essential Role for the dsRNA-Dependent Protein Kinase PKR in Innate Immunity to Viral Infection," Immunity, Jul. 2000, 13(1):129-141.
Belen'Kii et al., "Multiple drug effect analysis with confidence interval," Antiviral Research, 1994, 25:1-11.
Bellone et al., Annali di Chimica, 1964, V5 N54, 510-519, English summary on first page.
Blight et al., "Efficient Initiation of HCV RNA Replication in Cell Culture," Science, Dec. 8, 2000, 290:1972-1974.
Blight et al., "Efficient Replication of Hepatitis C Virus Genotype 1a RNAs in Cell Culture," Journal of Virology, Mar. 2003, 77(5):3181-3190.
Boyer et al., "Synthesis and photosynthetic inhibition activity of substituted 5-(bis-trifluoromethyl)methyl)-2-aminothiazoles," Journal of Fluorine Chemistry, 2006, 127:1522-1527.
Broekhuysen et al,. "Nitazoxanide: pharmacokinetics and metabolism in man," International Journal of Clinical Pharmacology and Therapeutics, 2000, 38(8):387-394.
Burger et al., "Isoterism and bioisoterism in drug design," Progress in Drug Research, Basel, 1991, 287-371.
Carr et al., "The lack of RNA-dependent protein kinase enhances susceptibility of mice to genital herpes simplex virus type 2 infection," Immunology, 2006, 118(4):520-526.
Chen et al., "The Natural History of Hepatitis C Virus (HCV) Infection," Int. J. Med. Sci., 2006, 3:47-52.
Database Biosis [Online], Biosciences Information Service, Philadelphia, PA, US May 2008, Callan et al., "Nitazoxanide and tizoxanide inhibit EHV-1 and influenza type A virus replication in vitro," XP009513576, Satabase accession No. PREV200800479437, Journal of Veterinary Internal Medicine, May 2008, 22(3):738, $26^{th}$ Annual Forum of the American College of Veterinary Internal Medicine, San Antonio, TX, Jun. 4-7, 2008.
Database Caplus [Online] Chemical Abstract Service, XP002498889, Database Accession No. 2000:53572 abstract of WO 00/02851, 3 pages.
Database Caplus [Online] Chemical Abstract Service, XP002498890, Database Accession No. 2003:918699, abstract of JP2003 335680 A, 1 page.
Database Caplus [Online] Chemical Abstract Service, XP002498891, Database Accession No. 1964:468902, 1 page abstract of Bellone et al., "New substituted acetophenones and their derivatives," Annali di Chimica, Societa Chimia Italiana, Rome, Italy, vol. 5, No. 54, Jan. 1, 1964, 510-519.
Database Caplus [Online] Chemical Abstract Service, XP002498892, Database Accession No. 2000:53572 abstract of WO 00/26202, 3 pages.
Database Registry [Online] Chemical Abstracts Service, Columbus, Ohio, US, 2000, XP002684230, retrieved from STN accession No. 304864-25-3, compounds 304864-25-3.
Elazar et al., "The Anti-Hepatitis C Agent Nitazoxanide Induces Phosphorylation of Eukaryotic Initiation Factor $2\alpha$ via Protein Kinase Activated by Double-Stranded RNA Activation," Gastroenterology, 2009, 137(5):1827-1835.
Fox et al., "Nitazoxanide: A New Thiazolide Antiparasitic Agent," Review of Anti-Infective Agents, Apr. 15, 2005, 40:1173-1180.
Garcia et al., "Impact of Protein Kinase PKR in Cell Biology: from Antiviral to Antiproliferative Ation," Microbiology and Molecular Biology Reviews, Dec. 2006, 70(4):1032-1060.
Giocometti et al., "Activity of nitazoxanide alone and in combination with azithromycin and rifabutin against *Cryptosporidium parvum* in cell culture," Journal of Antimicrobial Chemotherapy, 2000, 45:453-456.
Hoffman et al., "Antiparasitic Drug Nitazoxanide Inhibits the Pyruvate Oxidoreductases of *Helicobacter pylori*, Selected Anaerobic Bacterial and Parasites, and *Campylobacter jejuni*," Antimicrobial Agents and Chemotherapy, Mar. 2007, 51(3):868-876.
Hyojun Biseibutugaku (Microbiological Standard), Editorial supervision of Rinji Kawana, Igaku-Shoin Ltd., 1996, $6^{th}$ Edition, p. 392.
International Search Report and Written Opinion dated Aug. 23, 2010, in PCT/US2010/039638, 11 pages.
International Search Report and Written Opinion dated Jul. 9, 2010, in corresponding PCT/US2010/034319, 10 pages.
International Search Report dated Oct. 17, 2008, in PCT/US2008/071990, 5 pages.
Iyer et al., "Phosphorothioate Di- and Trinucleotides as a Novel Class of Anti-Hepatitis B Virus Agents," Antimicrobial Agents and Chemotherapy, Jun. 2004, 48(6):2199-2205.
Kabanov, Alexander V., "Polymer Genomics: An Insight into Pharmacology and Toxicology of Nanomedicines," Adv. Drug Deliv. Rev., Dec. 30, 2006, 58(15):1597-1621.
Korba et al., "Antisense oligonucleotides are effective inhibitors of hepatitis B virus replication in vitro," Antiviral Research, 1995, 28:225-242.
Korba et al., "Nitazoxanide, tizoxanide and other thiazoles are potent inhibitors of hepatits B virus and hepatitis C virus replication," Antiviral Research, 2008, 77:56-63.

(56) References Cited

OTHER PUBLICATIONS

Korba et al., "Potential for Hepatitis C Virus Resistance to Nitazoxanide or Tizoxanide," Antimicrobial Agents and Chemotherapy, Nov. 2008, 52(11):4069-4071.
Korba et al., "Use of a standardized cell culture assay to assess activities of nucleoside analogs against hepatitis B virus replication," Antiviral Research, 1992, 19:55-70.
Lavanchy, D., "Hepatitis B virus epidemiology, disease burden, treatment, and current and emerging prevention and control measures," Journal of Viral Hepatitis, 2004, 11:97-107.
Lerner et al., "Valacyclovir Treatment in Epstein-Barr Virus Subset Chronic Fatigue Syndrom: Thirty-six Months Follow-up," In Vivo, 2007, 21(5):707-714.
Lipunova et al., "Fluorine-Containing Heterocycles: XII. Fluorine-Containing Quinazolin-4-ones and Azolo[α]quinazolinone Derivatives," Russian Journal of Organic Chemistry, 2005, 41(7):1071-1080.
Locarnini, Stephen M.D., Ph.D., "Molecular Virology of Hepatitis B Virus," Seminars in Liver Disease, 2004, 24(Suppl. 1):3-10.
Masihi et al., "Low dose oral combination chemoprophylaxis with oseltamivir and amantadine for influenza A virus infections in mice," J. Chemother., 2007, 19(3):295-303; PubMed abstract PMID:17594925.
Minor et al., "Double-Stranded RNA-Activated Protein Kinase Regulates Early Innate Immune Responses During Respiratory Syncytial Virus Infection," Journal of Interferon & Cytokine Research, Apr. 2010, 30(4):263-272.
Monto et al., Arch. Intern. Med., Nov. 27, 2000, 160(21):3243-3247.
Montalto et al., American Family Physician, 2003, 67(1):111-118.
Mueller et al., "In Vitro Effects of Thiazolides on *Giardia lamblia* WB Cline C6 Cultured Axenically and in Coculture with Caco2 Cells," Antimicrobial Agents and Chemotherapy, Jan. 2006, 50(1):162-170.
Musher et al., "Nitazoxanide for the Treatment of *Clostridium difficile* Colitis," CID, Aug. 15, 2006, 43:421-427.
Okuse et al., "Enhancement of antiviral activity against hepatitis C virus in vitro by interferon combination therapy," Antiviral Research, 2005, 65:23-34.
Ortiz et al., "Randomized clinical study of nitazoxanide compared to metronidazole in the treatment of symptomatic giardiasis in children from Northern Peru," Ailment Pharmacol. Ther., 2001, 15:1409-1415.
Pankuch et al., "Activities of Tizoxanide and Nitazoxanide Compared to Those of Five Other Thiazoles and Three Other Agents against Anaerobic Species," Antimicrobial Agents and Chemotherapy, Mar. 2006, 50(3):1112-1117.
Patani et al., "Bioisoterism: A Rational Approach in Drug Design," Chem. Rev., 1996, 96(8):3147-3176.
Poland et al., "Influenza Virus Resistance to Antiviral Agents: A Plea for Rational Use," CID, May 1, 2009, 48:1254-1256.
Rao et al., "Design, Synthesis, and Biological Evaluation of 6-Substituted-3-(4-methanesulfonylphenyl)-4-phenylpyran-2-ones: A Novel Class of Diarylheterocyclic Selective Cyclooxygenase-2 Inhibitors," J. Med. Chem., 2003, 46:4872-4882.
Rossignol et al., "Effect of nitazoxanide for treatment of severe rotavirus diarrhea: randomized double-blind placebo-controlled trial," The Lancet, Jun. 13, 2006 online, 1-6.
Rossignol et al., "Effect of Nitazoxanide in Diarrhea and Enteritis Caused by *Cryptosporidium* Species," Clinical Gastroenterology and Hepatology, 2006, 4:320-324.
Rossignol et al., "Effect of Nitazoxanide in Persistent Diarrhea and Enteritis Associated with *Blastocystis hominis*," Clinical Gastroenterology and Hepatology, 2005, 3:987-991.
Rossignol et al., "Effect of Nitazoxanide in Treating Rotavirus Gastroenteritis in Hospitalized Pediatric Patients," Gastroenterology, 2006, 130(4,Suppl.2):A-01, 10.
Rossignol et al., "Nitazoxanide in the treatment of viral gastroenteritis: a randomized double-blind placebo-controlled clinical trial," Aliment. Pharacol. Ther., 2006, 24:1423-1430.
Rossignol et al., "Thiazolides, a New Class of Anti-influenza Molecules Targeting Viral Hemagglutinin at the Post-translation Level," J. Biol. Chem., Oct. 23, 2009, 284(43):29798-29808.
Rossignol et al., "Treatment of Diarrhea Caused by *Giardia intestinalis* and *Entamoeba histolytica* or *E. dispar*. A Randomized, Double-Blind, Placebo-Controlled Study of Nitazoxanide," J. Infect. Diseases, 2001, 184:381-384.
Santoro et al., "Thoazolides: A New Class of Broad-Spectrum Antiviral Drugs Targeting Virus Maturation," Antiviral Research, Program and Abstracts, The Twentieth International Conference on Antiviral Research, 2007, 74:A31 (11).
Schiavi et al., "Preparation of N-Tert-butoxycarbonylthiourea opens the way to protected 2-aminothiazoles," Synthetic Communications, 2002, 32(11):1671-1674.
Seikagaku Jiten (Dictionary of Biochemistry), Editorial supervision of Kazutomo Imabori et al., Tokyo Kagaku Dojin Co. Ltd., 1998, $3^{rd}$ Edition, pp. 552, 798 and 1462.
Sells et al., "Replicative Intermediates of Hepatitis B Virus in HepG2 Cells That Produce Infectious Virions," J. Virol., Aug. 1988, 62(8):2836-2844.
Stockis et al., "Nitazoxanide pharmacokinetics and tolerability in man during 7 days of 0.5 g and 1 g b.i.d. dosing," International Journal of Clinical Pharmacology and Therapeutics, 2002, 40(5):221-227.
Tellinghuisen et al., "Structure of the zinc-binding domain of an essential component of the hepatitis C virus replicase," Nature Letters, 2005, 435:374-379.
Teran et al., "Nitozoxanide vs. probiotics for the treatment of acute rotavirus diarrhea in children: a randomized, single-blind, controlled trial in Bolivian children," International Journal of Infectious Diseases, 2009, 13:518-523.
Tomei et al., "HCV antiviral resistance: the impact of in vitro studies on the development of antiviral agents targeting the viral NS5B polymerase," Antiviral Chemistry & Chemotherapy, 2005, 16:225-245.
Tong et al., "Identification and analysis of fitness of resistance mutations against the HCV protease inhibitor SCH 503034," Antiviral Research, 2006, 70:26-38.
Wallace et al., "Human Herpesviruses in Chronic Fatigue Syndrome," Clinical and Diagnostic Laboratory Immunology, Mar. 1999, 6(2):216-223.
Wong et al., "Update of viral hepatitis: 2005," Current Opinion in Gastroenterology, 2006, 22:241-247.
Yim et al., "Evolution of Multi-Drug Resistant Hepatitis B Virus During Sequential Therapy," Hepatology, Sep. 2006, 44(3):703-712.
Ziegler et al., "2-Aminothiazolesulfonamides," J. Org. Chem., 1960, 25:1454-1455.
Callan et al., "Nitazoxanide and tizoxanide inhibit EHV-1 and influenza Type A virus replication in vitro," Journal of Veterinary Internal Medicine, May 2008, 22(3):738, $26^{th}$ Annual Forum of the American College of Veterinary Internal Medicine, San Antonio, TX, Jun. 4-7, 2008, Abstract 126.

\* cited by examiner

COMPOUNDS AND METHODS FOR TREATING INFLUENZA

CROSS-REFERENCE TO RELATED APPLICATIONS

This application is a Continuation of U.S. application Ser. No. 15/814,949, filed Nov. 16, 2017, which is a Continuation of U.S. application Ser. No. 15/133,534, filed Mar. 16, 2015, which is a Continuation of U.S. application Ser. No. 14/658,409, filed Mar. 16, 2015, which is a Continuation of U.S. application Ser. No. 12/821,571, filed Jun. 23, 2010, which claims priority from U.S. Provisional Application No. 61/220,891, filed Jun. 26, 2009, the entire contents of which are incorporated herein by reference.

BACKGROUND

This invention is directed to methods and products employing thiazolides to treat and prevent influenza infection.

Influenza, a highly contagious acute respiratory illness affecting all age groups, causes about 36,000 deaths and over 226,000 hospitalizations per year in the United States alone. Classified (as types A, B, and C), according to antigenic differences in their nucleoprotein and matrix protein, the influenza viruses are enveloped, negative-stranded RNA viruses; the A type is the most important clinically. The many subtypes of influenza A virus differ in their two surface glycoproteins, hemagglutinin ("HA") and neuraminidase ("NA"), which are the main targets of the protective immune response, and are labeled according to the type of hemagglutinin (denoted with an H number) and neuraminidase (denoted with an N number). HA and NA vary continuously as a result of antigenic drift and antigenic shift. Sixteen H subtypes (or "serotypes") and nine N subtypes are known.

The emergence of highly pathogenic influenza A virus strains, such as the new H1N1 swine influenza, represents a particularly serious threat to global human health. In addition to surveillance and early diagnosis, efforts to control emerging influenza strains have emphasized the development of both effective vaccines and novel antiviral drugs.

Influenza A virus hemagglutinin is a trimeric glycoprotein that contains 3-9 N-linked glycosylation sequons per subunit, depending on the strain. HA is initially synthesized and core-glycosylated in the endoplasmic reticulum as a 75-79 kDa precursor (HA0) which assembles into noncovalently linked homo-trimers. The trimers are rapidly transported to the Golgi complex and reach the plasma membrane, where HA insertion initiates the process of assembly and maturation of the newly formed viral particles. Just prior to or coincident with insertion into the plasma membrane, each trimer subunit is proteolytically cleaved into two glycoproteins, HA1 and HA2, which remain linked by a disulfide bond.

SUMMARY

This invention concerns methods of treating and preventing viral infection by blocking the maturation of the viral hemagglutinin at a stage preceding resistance to endoglycosidase digestion. Treatment and prevention are carried out by administering a compound of formula I, or a pharmaceutically acceptable salt thereof, alone or in combination with other agents. Compounds of formula I exhibit antiviral activity via the novel mechanism of selectively blocking the maturation of the viral surface protein HA, thereby impairing intracellular trafficking and insertion into the host cell plasma membrane. Preliminary results suggest that compounds of formula I constitute a new class of antiviral drugs effective against influenza A infection. The present invention also provides a product containing a compound of formula I, or a pharmaceutically acceptable salt thereof, and an effective amount of an additional antiviral agent, or of an immunostimulant, or of a vaccine, as a combined preparation for separate, simultaneous, or sequential use in antiviral therapy.

BRIEF DESCRIPTION

This invention is directed to methods, pharmaceutical compositions, and combined preparations employing thiazolides of formula I for treating and preventing influenza infection by inhibiting influenza virus HA maturation. In the combined preparations, pharmaceutical compositions and methods of treating, according to the present invention, the antiviral agent may comprise 1 to 4 compounds or preparations, and may also include a vaccine and/or an immunostimulant.

In one embodiment, this invention provides or contemplates a pharmaceutical composition comprising a therapeutically effective amount of a compound of formula I or a pharmaceutically acceptable salt or ester thereof and a pharmaceutically acceptable carrier.

In another embodiment, this invention provides or contemplates a combination, useful for treating influenza, comprising a compound of formula I, or pharmaceutically acceptable salt thereof, and another antiviral agent.

In a more specific embodiment, this invention provides or contemplates a combination, useful for treating influenza, comprising a compound of formula I, or pharmaceutically acceptable salt thereof, and a neuraminidase inhibitor.

In another more specific embodiment, this invention provides or contemplates a combination, useful for treating influenza, comprising a compound of formula I, or pharmaceutically acceptable salt thereof, and an immunostimulant.

In another more specific embodiment, this invention provides or contemplates a combination, useful for treating influenza, comprising a compound of formula I, or pharmaceutically acceptable salt thereof, and PEGylated interferon.

In another more specific embodiment, this invention provides or contemplates a combination, useful for treating influenza, comprising a compound of formula I, or pharmaceutically acceptable salt thereof, and a recombinant sialidase fusion protein.

In another more specific embodiment, this invention provides or contemplates a combination, useful for treating influenza, comprising a compound of formula I, or pharmaceutically acceptable salt thereof, and a vaccine.

In another more specific embodiment, this invention provides or contemplates a combination, useful for treating influenza, comprising a compound of formula I, or pharmaceutically acceptable salt thereof, and an antisense oligonucleotide.

In another more specific embodiment, this invention provides or contemplates a combination, useful for treating influenza, comprising a compound of formula I, or pharmaceutically acceptable salt thereof, and another antiviral agent, where the two agents are to be administered substantially simultaneously.

In another more specific embodiment, this invention provides or contemplates a combination, useful for treating influenza, comprising a compound of formula I, or pharmaceutically acceptable salt thereof, and another antiviral agent, where the two agents are to be administered sequentially.

In another embodiment, this invention provides methods of treating and preventing viral infection by administering a compound of formula I, or pharmaceutically acceptable salt thereof.

In another embodiment, this invention provides methods of treating and preventing viral infection by administering a compound of formula I, or pharmaceutically acceptable salt thereof, in combination with an immunostimulant.

In another embodiment, this invention provides methods of treating and preventing viral infection by administering a compound of formula I, or pharmaceutically acceptable salt thereof, in combination with a neuraminidase inhibitor.

In another embodiment, this invention provides methods of treating and preventing viral infection by administering a compound of formula I, or pharmaceutically acceptable salt thereof, in combination with a vaccine.

In another embodiment, this invention provides methods of treating and preventing viral infection by administering a compound of formula I, or pharmaceutically acceptable salt thereof, in combination with an antisense oligonucleotide.

In another embodiment, this invention provides methods of treating and preventing viral infection by administering a compound of formula I, or pharmaceutically acceptable salt thereof, in combination with an adamantine analogue.

In another embodiment, this invention provides a combination pack or kit, useful for treating influenza, comprising a compound of formula I, or pharmaceutically acceptable salt thereof, and a neuraminidase inhibitor.

In another embodiment, this invention provides a combination pack or kit, useful for treating influenza, comprising a compound of formula I, or pharmaceutically acceptable salt thereof, and an immunostimulant.

In another embodiment, this invention provides a combination pack or kit, useful for treating influenza, comprising a compound of formula I, or pharmaceutically acceptable salt thereof, and an adamantine analogue.

In another embodiment, this invention provides a combination pack or kit, useful for treating influenza, comprising a compound of formula I, or pharmaceutically acceptable salt thereof, and a recombinant sialidase fusion protein.

In another embodiment, this invention provides a combination pack or kit, useful for treating influenza, comprising a compound of formula I, or pharmaceutically acceptable salt thereof, and an antisense oligonucleotide.

DETAILED DESCRIPTION

As used herein, the following terms have the meanings indicated.

Unless otherwise indicated, the term "a" means "one or more".

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The terms "combination," "combination therapy," and "co-therapy" embrace the administration of a compound of formula I, and another agent as part of a specific treatment regimen intended to provide a beneficial effect from the coordinated action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" generally is not intended to encompass the administration of two or more of these therapeutic agents as part of separate monotherapy regimens that incidentally and arbitrarily result in the combinations of the present invention. "Combination therapy" is intended to include administration of therapeutic agents in either a substantially simultaneous manner or in a sequential manner. Substantially simultaneous administration can be accomplished, for example, by administering a single capsule containing a fixed ratio of therapeutic agents or by administering single capsules for each of the therapeutic agents. Both sequential and substantially simultaneous administration of therapeutic agents can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The order in which the therapeutic agents are administered may be critical or it may be non-critical. "Combination therapy" also can embrace the administration of the therapeutic agents as described above in further combination with other biologically active ingredients (such as, but not limited to, different antiviral agents, vaccines, or immunostimulants), as well as non-drug therapies, including nutritional supplements.

The term "salts" is used in its broadest sense. For example, the term salts includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, halides, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane sulfonate, lactate, maleate, methanesulfonate, 2-naphthalenesulfonate, nicotinate, oxalate, thiocyanate, tosylate, and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The terms "therapeutically acceptable salt," and "pharmaceutically acceptable salt," as used herein, represent both salts and zwitterionic forms of the compounds of the present invention which are water or oil-soluble or dispersible; which are suitable for treatment of diseases without undue toxicity, irritation, and allergic response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzene sulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethane sulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxyl, phenol or similar group with a suitable base such as a metal hydroxide, carbonate, or bicarbonate, or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "solvates" is used in its broadest sense. For example, the term solvates includes hydrates formed when a compound of the present invention contains one or more bound water molecules.

The terms "alkylcarbonyl" and "alkanoyl," as used herein, refer to an alkyl group attached to the parent molecular moiety through a carbonyl group. Examples of such groups include methylcarbonyl, also known as acetyl; ethylcarbonyl, also known as propionyl; and 2-methyl-cyclopentylcarbonyl, etc.

The term "acyl," as used herein, refers to a carbonyl attached to an alkyl, alkenyl, aryl, heteroaryl, heterocycloalkyl, or any other moiety where the atom attached to the carbonyl is carbon. An "acetyl" group refers to a —C(O)CH3 group. Examples of acyl groups include alkanoyl groups such as formyl, acetyl, and propionyl, aroyl groups such as benzoyl, and mixed alkyl-aryl groups such as cinnamoyl.

The term "acylamino" refers to an amino radical substituted with an acyl group. One example of an "acylamino" radical is acetylamino (CH3C(O)NH—); another is benzoyl amino.

The term "alkenyl," as used herein, refers to a straight-chain, branched-chain, or cyclic unsaturated hydrocarbon radical, or a radical containing any combination of straight-chain or branched-chain, and cyclic moieties, having one or more double bonds and containing from 2 to 20 carbon atoms, or, in the case of cyclic moieties, having from 3 to 20 ring members. In many embodiments, alkenyl groups comprise from 2 to 6 carbon atoms. The term "alkenyl groups" is used in its broadest sense. For example, the term "(C2-C8) alkenyl groups" embraces straight, branched, and cyclic hydrocarbon radicals containing 2 to 8 carbon atoms having at least one double bond. Examples of suitable alkenyl radicals include ethenyl, also known as vinyl, propenyl, iso-propenyl, butenyl, iso-butenyl, sec-butenyl, tert-butenyl, 1,3-butadienyl, n-pentenyl, n-hexenyl, cycloalkenyl radicals such as cyclohexenyl and 1,3-cyclopentadienyl, cycloalkenylalkyl radicals such as cyclohexenylmethyl, alkenylcycloalkyl radicals such as methylenecyclohexyl, and the like.

Alkenylene refers to a carbon-carbon double bond system attached at two or more positions such as ethenylene [(—CH=CH—), (—C::C—)].

The term "alkoxy," as used herein, refers to an alkyl ether radical, wherein the term alkyl is as defined herein. Examples of suitable alkyl ether radicals include methoxy, ethoxy, n-propoxy, isopropoxy, n-butoxy, iso-butoxy, sec-butoxy, tert-butoxy, cyclopentoxy, and the like.

The term "alkoxyalkoxy," as used herein, refers to one or more alkoxy groups attached to the parent molecular moiety through another alkoxy group. Examples include ethoxyethoxy, methoxypropoxyethoxy, ethoxypentoxyethoxyethoxy and the like.

The term "alkoxyalkyl," as used herein, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkoxycarbonyl," as used herein, refers to an alkoxy group attached to the parent molecular moiety through a carbonyl group. Examples of such "alkoxycarbonyl" groups include methoxycarbonyl, ethoxycarbonyl, propoxycarbonyl, butoxycarbonyl and hexyloxycarbonyl.

The term "alkoxycarbonylalkyl" refers to radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "alkyl," as used herein, refers to a straight-chain, branched, or cyclic alkyl radical, or a radical consisting of any combination of straight, branched, and/or cyclic radicals, which is a saturated aliphatic hydrocarbon group containing from 1-20 carbon atoms. In many embodiments, alkyl groups comprise 1-10 carbon atoms. In many other embodiments, alkyl groups comprise 1-6 carbon atoms. The term "alkyl groups" is used in its broadest sense. Alkyl groups may be optionally substituted as defined herein. Examples of alkyl radicals include methyl, ethyl, n-propyl, isopropyl, cyclopropyl, cyclopropylmethyl, n-butyl, isobutyl, sec-butyl, tert-butyl, cyclobutyl, pentyl, neopentyl, iso-amyl, hexyl, cyclohexyl, trans-1,2-di-ethylcyclohexyl, octyl, nonyl and the like. For example, the abbreviation "(C1-C6)-alkyl groups" includes (C3-C6)-cycloalkyl groups as well as straight and branched alkyl groups, and "O(C1-C8)-alkyl groups" includes the straight-chain O(C1-C8)-alkyl groups, branched O(C1-C6")-alkyl groups, and cyclic O(C1-C6)-alkyl groups.

The term "alkylene," as used herein, refers to a saturated aliphatic group derived from a straight or branched chain saturated hydrocarbon attached at two or more positions, such as methylene (—CH2-), ethylene, and 1,3-cyclobutylene.

The term "alkylamino," as used herein, refers to an amino group attached to the parent molecular moiety through an alkyl group.

The term "alkylaminocarbonyl" as used herein, refers to an alkylamino group attached to the parent molecular moiety through a carbonyl group. Examples of such radicals include N-methylaminocarbonyl and N,N-dimethylcarbonyl.

The term "alkylidene," as used herein, refers to an alkenyl group in which one carbon atom of the carbon-carbon double bond belongs to the moiety to which the alkenyl group is attached.

The term "alkylsulfinyl," as used herein, refers to an alkyl group attached to the parent molecular moiety through a sulfinyl group. Examples of alkylsulfinyl groups include methylsulfinyl, ethylsulfinyl, butylsulfinyl and hexylsulfinyl.

The term "alkylsulfonyl," as used herein, refers to an alkyl group attached to the parent molecular moiety through a sulfonyl group. Examples of alkylsulfinyl groups include methanesulfonyl, ethanesulfonyl, tert-butanesulfonyl, and the like.

The term "alkylthio," as used herein, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "alkynyl," as used herein in its broadest sense, refers to a straight-chain, branched chain, or cyclic unsaturated hydrocarbon radical, as well as a radical which contains any combination of straight, branched, and/or cyclic radicals, having one or more carbon-carbon triple bonds and containing from 2 to 20 carbon atoms. In many embodiments alkynyl groups contain from 2 to 6 carbon atoms. In many other embodiments alkynyl groups contain from 2 to 4 carbon atoms. "Alkynylene" refers to a carbon-carbon triple bond attached at two positions such as ethynylene (—C:::C—, —C≡C—). For example, (C2-C8) alkynyl groups embraces straight, branched, and cyclic hydrocarbon chains containing 2 to 8 carbon atoms having at least one triple bond, and the term includes but is not limited to substituents such as ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like, unless otherwise indicated.

The term "amido," as used herein, refers to an amino group as described below attached to the parent molecular moiety through a carbonyl or sulfonyl group. The term "C-amido" as used herein, refers to a —C(=O)—NR2 group with R as defined herein. The term "N-amido" as used herein, refers to a RC(=O)NH— group, with R as defined herein.

The term "amino," as used herein, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxyalkyl, nitro, and oxo.

The term "aminoalkyl," as used herein, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, refer to an amino-substituted carbonyl group, wherein the amino group can be a primary or secondary amino group containing substituents selected from alkyl, aryl, aralkyl, cycloalkyl, cycloalkylalkyl radicals, and the like.

The term "aminocarbonylalkyl," as used herein, refers to an aminocarbonyl radical attached to an alkyl radical, as described above. An example of such radicals is aminocarbonylmethyl. The term "amidino" denotes an —C(NH)NH2 radical. The term "cyanoamidino" denotes an —C(N—CN) NH2 radical.

The term "aralkenyl" or "arylalkenyl," as used herein, refers to an aryl group attached to the parent molecular moiety through an alkenyl group.

The term "aralkoxy" or "arylalkoxy," as used herein, refers to an aryl group attached to the parent molecular moiety through an alkoxy group.

The term "aralkyl" or "arylalkyl," as used herein, refers to an aryl group attached to the parent molecular moiety through an alkyl group.

The term "aralkylamino" or "arylalkylamino," as used herein, refers to an arylalkyl group attached to the parent molecular moiety through a nitrogen atom, wherein the nitrogen atom is substituted with hydrogen.

The term "aralkylidene" or "arylalkylidene," as used herein, refers to an aryl group attached to the parent molecular moiety through an alkylidene group The term "aralkylthio" or "arylalkylthio," as used herein, refers to an arylalkyl group attached to the parent molecular moiety through a sulfur atom.

The term "aralkynyl" or "arylalkynyl," as used herein, refers to an aryl group attached to the parent molecular moiety through an alkynyl group.

The term "aralkoxycarbonyl," as used herein, refers to a radical of the formula aralkyl-O—C(O)— in which the term "aralkyl," has the significance given above. Examples of an aralkoxycarbonyl radical are benzyloxycarbonyl ("Z" or "Cbz") and 4-methoxyphenylmethoxycarbonyl ("MOS").

The term "aralkanoyl," as used herein, refers to an acyl radical derived from an aryl-substituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl," as used herein, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "arylamino" as used herein, refers to an aryl group attached to the parent moiety through an amino group, such as N-phenylamino, and the like.

The terms "arylcarbonyl" and "aroyl," as used herein, refer to an aryl group attached to the parent molecular moiety through a carbonyl group.

The term "aryloxy," as used herein, refers to an aryl group attached to the parent molecular moiety through an oxygen atom.

The term "arylsulfonyl," as used herein, refers to an aryl group attached to the parent molecular moiety through a sulfonyl group.

The term "arylthio," as used herein, refers to an aryl group attached to the parent molecular moiety through a sulfur atom.

The terms "carboxy" or "carboxyl", whether used alone or with other terms, such as "carboxyalkyl", denotes —CO2H.

The terms "benzo" and "benz," as used herein, refer to the divalent radical C6H4=derived from benzene. Examples include benzothiophene and benzimidazole.

The term "carbamoyloxy," as used herein, refers to an amino-substituted carbonyl group attached to the parent molecular moiety through a oxygen atom (e.g. RR'NC(=O) O—), wherein the amino group can be a primary or secondary amino group containing substituents selected from alkyl, aryl, aralkyl, cycloalkyl, cycloalkylalkyl radicals and the like.

The term "O-carbamyl" as used herein, refers to a —OC (O)NR, group-with R as defined herein.

The term "C-linked" as used herein, refers to any substituent that is attached to the parent molecular moiety through a carbon-carbon bond.

The term "N-carbamyl" as used herein, refers to a ROC (O)NH— group, with R as defined herein.

The term "carbonate" as used herein, refers to a —O—C (=O)OR group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" such as a carboxylic acid salt derivative or ester derivative. An "O-carboxy" group refers to a RC(O)O— group, where R is as defined herein. A "C-carboxy" group refers to a —C(O)OR groups where R is as defined herein.

The term "cyano," as used herein, refers to the —CN group.

The term "cycloalkyl," as used herein, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2.2.2]octane, bicyclo[2.2.2]octane, bicyclo[1.1.1]pentane, camphor and bicyclo[3.2.1]octane.

The term "cycloalkenyl," as used herein, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkylalkyl," as used herein, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, refers to a carbonyloxy —(C=O)O— group bridging two moieties linked at carbon atoms. Examples include ethyl benzoate, n-butyl cinnamate, phenyl acetate and the like.

The term "ether," as used herein, refers to an oxy group bridging two moieties linked at carbon atoms.

The term "halo," or "halogen," as used herein, refers to fluorine, chlorine, bromine, or iodine.

The term "haloalkoxy," as used herein, refers to a haloalkyl group attached to the parent molecular moiety through an oxygen atom.

The term "haloalkyl," as used herein, refers to an alkyl radical having the meaning as defined above wherein one or more hydrogens are replaced with a halogen. Specifically included are monohaloalkyl, dihaloalkyl, perhaloalkyl, and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CHF—), difluoromethylene (—CF2-), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, refers to an aromatic five- or six-membered ring, where at least one atom is selected from the group consisting of N, O, and S, and the remaining ring atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxazolyl, benzofuranyl, benzimidazolyl, benzthiazolyl benzotriazolyl, cinnolinyl, furyl, imidazolyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], indazolyl, indolyl, isoxazolyl, isoquinolinyl, isothiazolyl, naphthyridinyl, oxadiazolyl [e.g., 1,2,4-oxadiazolyl, 1,3,4-oxadiazolyl, 1,2,5-oxadiazolyl, etc.], oxazolyl, isoxazolyl, purinyl, thiazolyl, isothiazolyl, thienopyridinyl, thienyl, thiadiazolyl [e.g., 1,2,4-thiadiazolyl, 1,3,4-thiadiazolyl, 1,2,5-thiadiazolyl, etc.], pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the groups as defined herein.

Examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl The term "heteroaralkyl" or "heteroarylalkyl," as used herein, refers to a heteroaryl group attached to the parent molecular moiety through an alkyl group.

The term "heteroaralkenyl" or "heteroarylalkenyl," as used herein, refers to a heteroaryl group attached to the parent molecular moiety through an alkenyl group.

The term "heteroaralkoxy" or "heteroarylalkoxy," as used herein, refers to a heteroaryl group attached to the parent molecular moiety through an alkoxy group.

The term "heteroaralkylidene" or "heteroarylalkylidene," as used herein, refers to a heteroaryl group attached to the parent molecular moiety through an alkylidene group.

The term "heteroaryloxy," as used herein, refers to a heteroaryl group attached to the parent molecular moiety through an oxygen atom.

The term "heteroarylsulfonyl," as used herein, refers to a heteroaryl group attached to the parent molecular moiety through a sulfonyl group.

The terms "heterocycloalkyl" and, interchangeably, "heterocyclyl," as used herein, each refer to a saturated, partially unsaturated, or fully unsaturated monocyclic, bicyclic, or tricyclic heterocyclic radical containing one or more heteroatoms as ring members, wherein each said heteroatom may be independently selected from the group consisting of nitrogen, oxygen, and sulfur, and wherein there are typically 3 to 8 ring members in each ring. Most commonly heterocyclic rings contain 5 to 6 ring members. In some embodiments of this invention heterocyclic rings contain 1 to 4 heteroatoms; in other embodiments, heterocyclic rings contain 1 to 2 heteroatoms. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, refers to a heterocycle group attached to the parent molecular moiety through an alkenyl group.

The term "heterocycloalkoxy," as used herein, refers to a heterocycle group attached to the parent molecular group through an oxygen atom.

The term "heterocycloalkylalkyl," as used herein, refers to an alkyl radical as defined above in which at least one hydrogen atom is replaced by a heterocycloalkyl radical as defined above, such as pyrrolidinylmethyl, tetrahydrothienylmethyl, pyridylmethyl and the like.

The term "heterocycloalkylidene," as used herein, refers to a heterocycle group attached to the parent molecular moiety through an alkylidene group.

The term "hydrazinyl" as used herein, refers to two amino groups joined by a single bond, i.e., —N—N—.

The terms "hydroxy" and "hydroxyl," as used herein, refer to the —OH group.

The term "hydroxyalkyl" as used herein, refers to a linear or branched alkyl group having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "hydroxyalkyl," as used herein, refers to a hydroxy group attached to the parent molecular moiety through an alkyl group.

The term "imino," as used herein, refers to =N—.

The term "iminohydroxy," as used herein, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein in such terms as "lower alkyl," means having 1, 2, 3, 4, 5, or 6 carbon atoms.

The term "mercaptoalkyl" as used herein, refers to an R'SR— group, where R and R' are as defined herein.

The term "mercaptomercaptyl" as used herein, refers to a RSR'S— group, where R is as defined herein.

The term "mercaptyl" as used herein, refers to an RS— group, where R is as defined herein.

The term "null" refers to a lone electron pair.

The term "nitro," as used herein, refers to —NO2.

The term "optionally substituted" means the anteceding group may be substituted or unsubstituted. "Substituted" means that one or more hydrogen atoms bound to carbon are replaced by "substituents." Substituents which are included within or contemplated by the term "optionally substituted" are: C1-3 alkyl, C3-6 cycloalkyl, C1-3 alkoxy, hydroxy, C1-3 alkanoyl, C1-3 alkoxy carbonyl, halo, phenyl, benzyl, phenoxy, benzoyl, pyridyl, amino, C1-3 alkyl amino, amido, C1-3 alkyl amido, cyano, C1-3 haloalkyl, and C1-3 perhaloalkyl. Two substituents may be joined together to form a fused four-, five-, six-, or seven-membered carbocyclic or heterocyclic ring consisting of zero to three heteroatoms, such as methylenedioxy, or ethylenedioxy. An optionally substituted group may be unsubstituted (e.g., —CH2CH3), fully substituted (e.g., —CF2CF3), monosubstituted (e.g., —CH2CH2F) or substituted at a level anywhere between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. All pendant aryl, heteroaryl, and heterocyclo moieties can be further optionally substituted with one, two, three, four, or five substituents independently selected from the groups listed above.

The terms "oxy" or "oxa," as used herein, refer to —O—.

The term "oxo" as used herein, refers to a doubly bonded oxygen =O.

The term "perhaloalkoxy" refers to an alkoxy group where all of the hydrogen atoms are replaced by halogen atoms.

The term "perhaloalkyl" as used herein, refers to an alkyl group where all of the hydrogen atoms are replaced by halogen atoms.

The term "phosphonate" as used herein, refers to the —P(=O)(OG)(OG1) group, where G and G1 are chosen from H, alkyl, alkenyl, alkynyl, aryl, heteroaryl, etc.

The term "phosphinate" as used herein, refers to the —P(=O)(G)(OG1) group, where G and G1 are chosen from H, alkyl, alkenyl, alkynyl, aryl, heteroaryl, etc.

The terms "sulfonate," "sulfonic acid," and "sulfonic," as used herein, refer the —SO3H group and its anion as the sulfonic acid is used in salt formation.

The term "sulfanyl," as used herein, refers to —S and ~S—.

The term "sulfinyl," as used herein, refers to —S(O)—.

The term "sulfonyl," as used herein, refers to —SO2-.

The term "N-sulfonamido" refers to a RS(=O)2NH— group with R as defined herein.

The term "S-sulfonamido" refers to a —S(=O)2NR2, group, with R as defined herein.

The terms "thia" and "thio," as used herein, refer to a —S— group or an ether wherein the oxygen is replaced with sulfur. The oxidized derivatives of the thio group, namely sulfinyl and sulfonyl, are included in the definition of thia and thio.

The term "thioether," as used herein, refers to a thio group bridging two moieties linked at carbon atoms.

The term "thiol," as used herein, refers to an —SH group.

The term "thiocarbonyl," as used herein, when alone includes thioformyl —C(S)H and in combination is a —C(S)— group.

The term "N-thiocarbamyl" refers to an ROC(S)NH— group, with R as defined herein.

The term "O-thiocarbamyl" refers to a —OC(S)NR, group with R as defined herein.

The term "thiocyanato" refers to a —CNS group.

The term "trihalomethanesulfonamido" refers to a X3CS(O)2NR— group with X is a halogen and R as defined herein.

The term "trihalomethanesulfonyl" refers to a X3CS(O)2- group where X is a halogen.

The term "trihalomethoxy" refers to a X3CO— group where X is a halogen.

The term "trisubstituted silyl," as used herein, refers to a silicone group substituted at its three free valences with groups as listed herein under the definition of substituted amino. Examples include trimethysilyl, tert-butyldimethylsilyl, triphenylsilyl and the like.

The term "urea," as used herein, refers to —N(R)C(=O)N(R)(R), with R as defined herein.

The term "carrier" is used in its broadest sense. For example, the term carrier refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition.

The present invention also relates to a pharmaceutical composition comprising, in a pharmaceutically acceptable carrier, an effective amount of at least one compound of the invention.

The term effective amount is used in its broadest sense. The term, for example, refers to the amount required to produce a desired effect.

DETAILED DESCRIPTION

Figure 1:
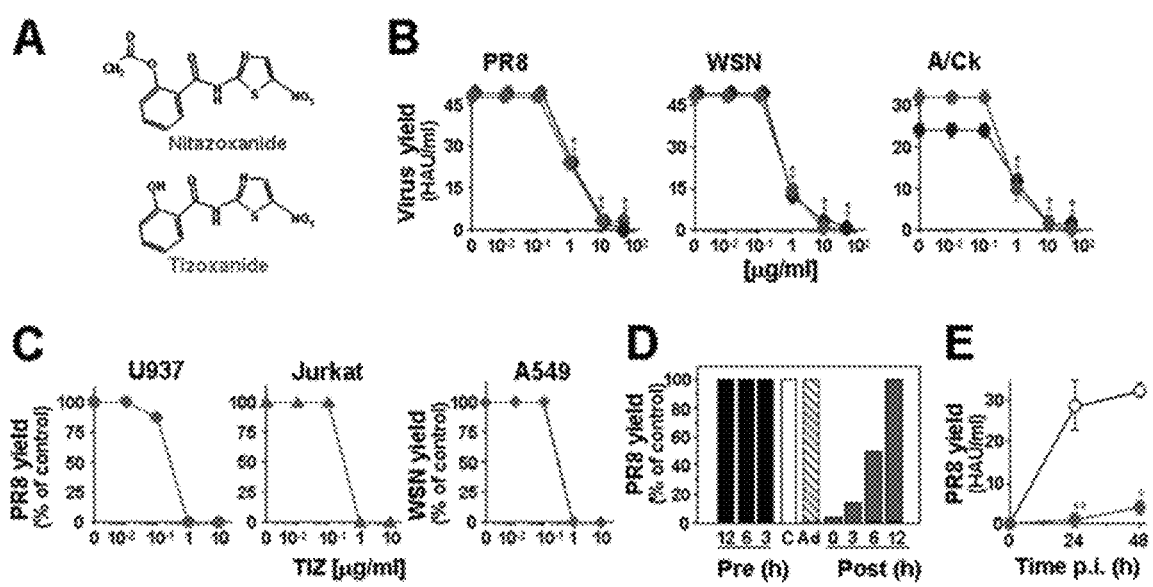
FIG. 1. Thiazolides inhibit influenza A virus replication acting at a post-entry level. A, structure of nitazoxanide (NTZ) and tizoxanide (TIZ). B, NTZ (blue circles) and TIZ (red circles) inhibit the replication of human (PR8, WSN) and avian (A/Ck) influenza A virus strains in MDCK cells. Virus yield was determined at 24 h p.i. C, antiviral activity of TIZ on influenza A PR8 virus in human monocytic U937 (●) and T-lymphoblastoid Jurkat (▲) cells, and WSN virus in human lung epithelial A549 cells (■). D, MDCK cells were treated with 10 μg/ml TIZ (filled bars) at the indicated times before infection (Pre), immediately after the adsorption period (Post), or only during the adsorption period (Ad, dashed bar). Empty bar represents untreated infected control (C). E, long-term antiviral activity of TIZ in PR8-infected MDCK cells treated with 10 μg/ml TIZ (filled circles) or vehicle (empty circles) after virus adsorption. B-E, virus yield, expressed in HAU/ml (B and E) or as percent of non-treated control (C and D), represents the mean±SD of duplicate samples from a representative experiment of three with similar results. *=P<0.01; **=P<0.05

In one embodiment, the present invention targets the maturation of the viral hemagglutinin and offers the opportunity to disrupt the production of infectious viral particles at a stage different from that afforded by the currently available anti-influenza drugs. In another embodiment, the inventions provides or contemplates methods of treating and preventing viral infection in humans and other mammals by administering effective amounts of compounds of formula I. One such compound is nitazoxanide (1), a licensed product in the United States for the treatment of infectious gastroenteritis that is currently undergoing phase II clinical trials in the United States and abroad for the treatment of chronic hepatitis C. The drug has been shown to be safe and effective even when given over a year, and phase II clinical studies could be initiated in the treatment of influenza at any time in the future. Clinical trials have recently demonstrated activity of commercially available pharmaceutical formulations of nitazoxanide in treating rotavirus gastroenteritis and chronic hepatitis B and C.

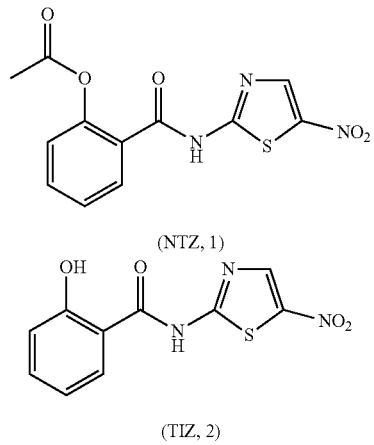

(NTZ, 1)

(TIZ, 2)

EXPERIMENTAL PROCEDURES

Materials and Methods

Materials

Nitazoxanide (NTZ, I), tizoxanide (TIZ, 2), and thiazolide analogs and reference compound swainsonine (SW) (Sigma-Aldrich) were dissolved in dimethylsulfoxide (DMSO). Tunicamycin (TM) and 1-deoxymannojirimicin (DMJ) (Sigma-Aldrich) were dissolved in aqueous solution.

Methods for Influenza Studies

Cell culture, treatment and transfection-Madin-Darby canine kidney (MDCK) cells, and human A549 alveolar type II-like epithelial, Jurkat Tlymphoblastoid and U397 monocytic leukemia cells were grown at 37° C. in a 5% CO2 atmosphere in RPMI 1640 (Invitrogen), supplemented with 10% fetal calf serum (FCS), 2 mM glutamine and antibiotics. Test compounds were added immediately after 1-hour adsorption period, and kept in the culture medium for the entire time of the experiment, unless differently specified. Controls received equal amounts of vehicle, which did not affect cell viability or virus replication. Cell viability was determined by the 3-(4,5-dimethylthiazol-2-yl)-2,5-diphenyltetrazolium bromide (MTT) to MTT formazan conversion assay (Sigma-Aldrich) as described previously. Microscopical examination of mock-infected or virus-infected cells was performed using a Leica DM-IL microscope and images were captured on a Leica DC 300 camera using Leica Image-Manager500 software.

For transfection experiments, MDCK cells plated in LabTekII coverglass chambers (Nunch-Thermo Fisher Scientific Inc.) were transiently transfected with green fluorescent protein (GFP)-tagged internalization-defective human low-density lipoprotein receptor (hLDLR) mutant (LDLR-A18-GFP plasmid, kindly provided by E. Rodriguez-Boulan, Cornell University New York, N.Y.), using Lipofectamine 2000 (Invitrogen) according to the manufacturer's instructions.

Virus preparation, infection and titration—Four different influenza A viruses, the mammalian H1N1 A/PR/8/34 (PR8) and A/WSN/33 (WSN), and H3N2 A/Firenze/7/03 (A/FI), and the H5N9 low-pathogenicity avian strain A/Ck/It/9097/97 (A/Ck), as well as influenza B virus, B/Parma/3/04 clinical isolate, were utilized for this study. A/Firenze/7/03, A/Ck/It/9097/97 and B/Parma/3/04 influenza viruses were a kind gift from Dr. Isabella Donatelli, Istituto Superiore di Sanita', Rome, Italy. The avian strain A/Ck/It/9097/97 was isolated after an initial passage of chicken organ homogenates into 10-day-old specific-pathogen-free (SPF) embryonated chicken eggs. Influenza A viruses were grown in the allantoic cavity of 8-day-old embryonated eggs. After 48 h at 37° C., the allantoic fluid was harvested and centrifuged at 5000 rpm for 30 min. to remove cellular debris, and virus titers were determined by hemagglutinin titration and plaque assay, according to standard procedures. Confluent cell monolayers were infected with influenza virus for 1 h at 37° C. at a multiplicity of infection (m.o.i.) of 5 HAU/105 cells, unless differently specified. After the adsorption period (time 0), the viral inoculum was removed, and cell monolayers were washed three times with phosphate-buffered saline (PBS). Cells were maintained at 37° C. in RPMI 1640 culture medium containing 2% fetal calf serum. For multistep virus growth curves, infected cells were incubated in the same medium containing 1 µg/ml trypsin IX (Sigma-Aldrich). Virus yield was determined 24 or 48 h post infection (p.i.) by hemagglutinin titration. For PR8 virus infectivity assay, MDCK cells grown on 96-well plates were inoculated with serial dilutions of viral suspension in the presence of 1 µg/ml trypsin for 48 h at 37° C., and TCID50 (50% tissue culture infective dose) was determined as described. Alternatively, virus titers were determined on MDCK cells by counting the numbers of fluorescent cells after infection and indirect immunofluorescence staining with antiinfluenza A/PR/8/34 antibodies (anti-PR8, a kind gift from E. Rodriguez-Boulan, Cornell University New York, N.Y.). Titers were correspondingly expressed as ffu (fluorescence-forming units)/ml.

Metabolic labeling, analysis of protein synthesis and Western Blot Mock-infected or influenza virus-infected cells were labeled with 10 µCi/ml of [35S]-methionine-cysteine ([35S]-Met/Cys, Redivue Pro-Mix 35S in vitro cell-labeling mix; GE Healthcare) for the indicated times after 30 min. starvation in methionine/cysteine-free medium. For pulse/chase experiments, cells were labeled [35S]-Met/Cys (100 µCi/ml) for 15 min., after 30 min. starvation in methionine/cysteine-free medium. At the end of pulse, cells were chased in complete medium containing 10 mM cold methionine and 1 mM cycloheximide for different times in the absence or presence of TIZ. The pulse/chase were terminated by placing the cells on ice. After cell lysis in RIPA buffer (150 mM NaCl, 10 mM Tris-HCl pH 7.5, 4 mM EDTA, 1% Triton X-100, 600 mM KCl), containing 1 mM phenylmethylsulphonyl fluoride (PMSF) and a protease inhibitor cocktail (PIC; Roche Diagnostics GmbH), samples containing the same amount of radioactivity were separated by SDS/PAGE (3% stacking gel, 10% resolving gel) and processed for autoradiography, as described. Autoradiographic patterns were visualized and quantified in Typhoon-8600 Imager (Molecular Dynamics, Amersham Pharmacia Biotech) and images were acquired using ImageQuant software (Amersham Pharmacia Biotech) (MDP analysis).

For analysis of proteins incorporated into virus particles, PR8-infected or mock-infected MDCK cells treated with TIZ, TM or vehicle after virus adsorption were labeled at 3 h p.i. with [35S]-Met/Cys (25 µCi/ml, 21 h-pulse) in the presence of the drugs. At 24 h p.i., cell culture supernatants were harvested and subjected to centrifugation at 13,000 rpm for 10 min. to remove cellular debris, and then ultracentrifugation at 45,000 rpm (Beckman XL-100K Ultracentrifuge, rotor 70.1Ti; Beckman Coulter Inc.) for 2 hours. The pellets containing viral particles were resuspended in Laemmli sample buffer and radiolabeled viral proteins were separated by 10% SDS-PAGE and examined by autoradiography, after exposure to Amplify™ Fluorographic Reagent (GE Healthcare). Autoradiographic patterns were visualized as described above.

For Western blot analysis, cells were lysed with cold high-salt extraction (HSB) buffer containing 2 mM dithiothreitol (DTT), 1 mM PMSF, 1 mM orthovanadate, 20 mM β-glycerophosphate, 1 mM p-nitrophenyl phosphate (pNPP) and PIC, or with RIPA buffer, containing 1 mM PMSF and PIC. Whole-cell extracts (30 µg) were separated by SDS-PAGE, blotted to nitrocellulose, and filters were incubated with polyclonal anti-phosphoSer51-eIF2α (p-eIF2α, Calbiochem), anti-eIF2α (FL-315, Santa Cruz Biotechnology), and anti-influenza A/PR/8/34 antibodies or monoclonal anti-HA (IVC102; Biodesign Inc.) and anti-Grp78/BiP (Stressgene) antibodies, followed by decoration with peroxidase-labeled anti-rabbit IgG or anti-mouse IgG (Super Signal detection kit; Pierce). Quantitative evaluation of proteins was determined by Versadoc-1000 analysis using the Quantity One software program, available through BIO-RAD Laboratories.

Immunoprecipitation of HA0 PR8-infected or mock-infected MDCK cells treated with 10 µg/ml TIZ or control diluent after virus adsorption were labeled at 5 or 6 h p.i. with [35S]-Met/Cys (70 µCi/ml, 4 h-pulse) after 30 min. starvation in methionine/cysteine-free medium. After lysis in RIPA buffer in the presence of PIC and 1 mM PMSF, cell debris were removed by cold centrifugation at 13,000 rpm for 10 min. Radiolabeled lysates (50 µl) were incubated with anti-HA monoclonal antibodies (IVC102; Biodesign Inc.) in RIPA buffer containing 1 mM PMSF, PIC and protein-A-Sepharose (Sigma-Aldrich) at 4° C. for 16 h. After centrifugation, pellets were washed 3 times with RIPA buffer, and eluted in Laemmli sample buffer (20) at 95° C. for 5 min. Immunoprecipitated samples were subjected to Endo-H digestion (as described below) and/or processed for SDS/PAGE (3% stacking gel, 10% resolving gel) and autoradiography, after exposure to Amplify™ Fluorographic Reagent. Autoradiographic patterns were visualized in Typhoon-8600 Imager and images were acquired as described above.

Analysis of hemagglutinin glycosylation, trimerization and processing Mock-infected or influenza virus-infected cells were labeled with 20 µCi/ml of [3H]-mannose or [3H]-glucosamine hydrochloride (GE Healthcare) for 4 hours at 6 h p.i., and then processed for SDS/PAGE (3% stacking gel, 10% resolving gel) and autoradiography, as described above. For endoglycosidase digestion experiments, MDCK cells were infected with PR8 influenza virus, washed free of unbound virus, and incubated in the presence or absence of 10 µg/ml TIZ. At 5 h p.i. cells were labeled with [35S]-Met/Cys (50 µCi/ml, 4 h-pulse) after 30 min. starvation in methionine/cysteine-free medium. At the end of pulse, the radioactive medium was removed and cells were placed on ice. After lysis in L buffer (100 mM NaCl, 10 mM Tris-HCl pH 7.5, 5 mM EDTA, 1% Triton X-100, 0.1% SDS) in the presence of PIC and 1 mM PMSF, and cold centrifugation at 13,000 rpm for 10 min, samples containing the same amount of radioactivity were processed for endoglycosydase H (Endo-H) or Peptide N-Glycosidase F (PNGase-F) digestion. For Endo-H digestion, samples immunoprecipitated with anti-HA monoclonal antibody (as described above) or nonimmunoprecipitated samples were incubated in 100 µl of 0.1% SDS and 140 mM β-mercaptoethanol in 100 mM sodium citrate (pH 5.5), and heated for 5 min at 95° C. After addition of 1 mM PMSF and PIC, samples were divided into two equal aliquots, and one aliquot was incubated with 5 mU Endo-H (Roche Diagnostics GmbH) for 16 h at 37° C. Peptide N-glycosidase digestion was performed with 500 U of PNGase-F, according to the manufacturer's protocol (New England BioLabs Inc.). Digestions were terminated with addition of Laemmli sample buffer. Samples were heated at 95° C. for 5 min before loading onto 10% SDS-PAGE gels. For analysis of trimer formations, crosslinking of HA was performed by adding 1:10 volume of DMSO containing 0.2 mM EGS [ethylene glycol bis(succinimidylsuccinate); Pierce] to whole-cell extracts from mock-infected and PR8-infected MDCK cells. After 15 min at 22° C., reactions were quenched by addition of glycine at a final concentration of 75 mM and samples were subjected to SDS-PAGE (6% resolving gel). The HA-crosslinked products were visualized by probing with monoclonal anti-HA antibodies or polyclonal anti-PR8.

Immunofluorescence microscopy PR8-infected MDCK and WSN-infected A549 cells grown on coverslips were fixed with 4% paraformaldehyde in phosphate-buffered saline for 20 min. at room temperature at 16 or 24 h p.i respectively. Mock-infected cells were processed similarly. Fixed cells were either incubated with anti-HA monoclonal antibodies (IVC102; Biodesign Inc.) for 1 h at 37° C. for plasma membrane staining, or were permeabilized with 0.1% TritonX100-PBS for 10 min. at room temperature and then incubated with monoclonal anti-HA and anti-p230 trans-Golgi (clone 15; BD Biosciences) or polyclonal anti-α-tubulin (11H10; Cell Signaling, Technology Inc.) antibodies for 1 h at 37° C., followed by decoration with Alexa Fluor488-conjugated (Molecular Probes-Invitrogen) or rhodamine-conjugated (Pierce) goat anti-mouse IgG, and rhodamine-conjugated goat anti-rabbit IgG (Pierce). Nuclei were stained with 4',6-diamidino-2-phenylindole (DAPI) or Hoechst 33342 (Molecular Probes, Invitrogen). Images were captured and deconvolved with a DeltaVision microscope (Applied-Precision) using the SoftWoRx-2.50 software (Applied-Precision). Control incubations demonstrated non cross-reactivity between the anti-immunoglobulin conjugates, or between the anti-immunoglobulin conjugate and the irrelevant primary antibody. Images of a representative experiment of three with similar results are shown.

For detection of plasma membrane targeting of human low-density lipoprotein receptor (hLDLR), MDCK cells plated in coverglass chambers were transiently transfected with GFPtagged internalization-defective hLDLR mutant (LDLR-A18-GFP plasmid) and, after 8 h, treated with TIZ (10 µg/ml) or vehicle for the following 16 h. After blocking protein synthesis with 100 µg/ml cycloheximide (Sigma-Aldrich) for 1 h, plasma membranes were stained using CellMask™ Orange plasma membrane stain (Molecular Probes, Invitrogen). After staining, cells were examined using a Leica DM-IL fluorescence microscope equipped with UV excitation filters. The images were captured with a Leica DC-300 camera using Leica Image-Manager500 software.

Hemadsorption assay—Mock- or PR8-infected MDCK cell monolayers were treated with TIZ, TM or vehicle after virus adsorption. At 5 h p.i., cells were washed three times with PBS, and incubated with 0.1% of human red blood cells (RBC) in PBS for 20 min. at 4° C. to inhibit neuraminidase activity. After removal of unbound erythrocytes by washing three times with PBS, RBC adsorbed on MDCK cell surface were detected by phase contrast microscopy. Images were captured with a Leica DMLB microscope equipped with a Leica DC300 camera, using Leica Image-Manager500 software. Adherent erythrocytes were lysed in 150 mM NH4Cl buffer for 2 h at room temperature and quantified by measuring hemoglobin absorbance at $\lambda=540$ nm.

Statistical analysis—Statistical analysis was performed using the Student's t test for unpaired data. Data are expressed as the mean+S.D. of duplicate samples. P values of <0.05 were considered significant.

Results

Figure 10:
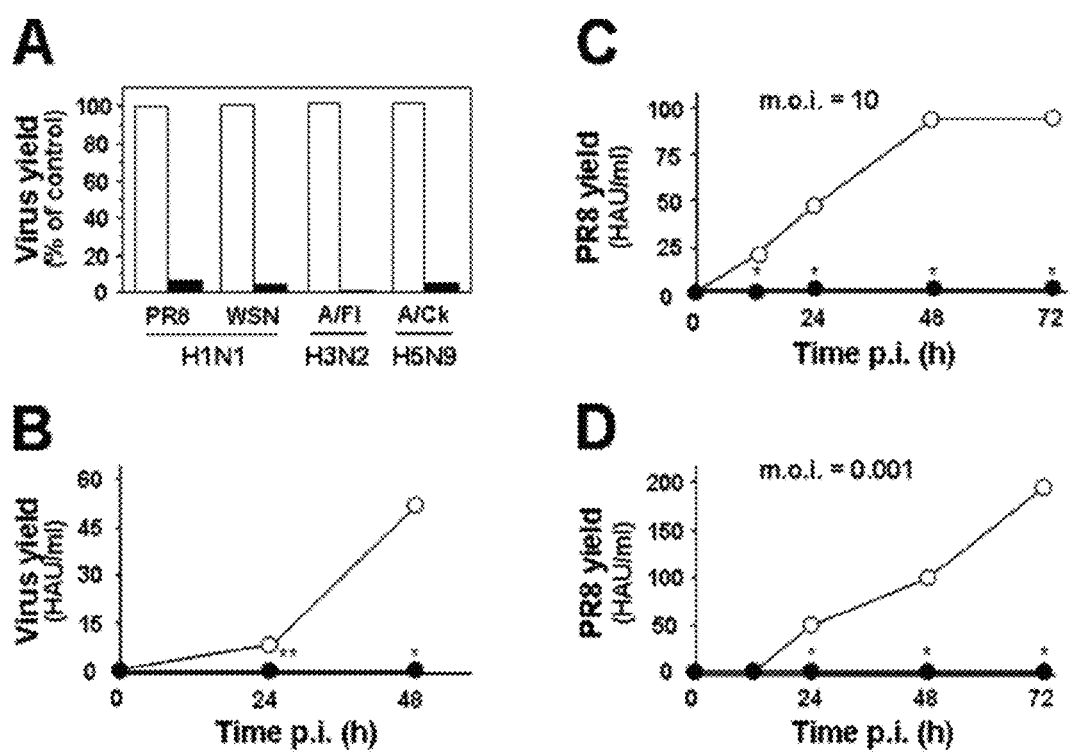
FIG. 10. Antiviral activity of tizoxanide against influenza A and B viruses. A, MDCK cells were infected with four different influenza A virus strains, the mammalian H1N1 PR8 and WSN, and H3N2 A/FI, and the H5N9 avian strain A/Ck at a m.o.i. of 10 HAU/105 cells, and treated with 10 µg/ml TIZ (filled bars) or vehicle (empty bars) immediately after the adsorption period. Virus yield was determined at 24 h p.i. B, long-term antiviral activity of TIZ in MDCK cells infected with influenza B virus (B/Parma/3/04) and treated with 10 µg/ml TIZ (●) or vehicle (M) after virus adsorption. C-D, single-step (C) and multistep (D) PR8 virus growth curves were performed on MDCK cells infected at an m.o.i. of 10 (C) or 0.001 (D) ffu/cell and treated with 10 µg/ml TIZ (●) or vehicle (M) as in A. Virus yield was determined at the indicated times p.i. (A-D) Virus yield, expressed as percent of untreated control (A) or in HAU/ml (B-D) represents the mean±SD of duplicate samples from a representative experiment of three with similar results. *=P<0.01; **=P<0.05.
Figure 11:
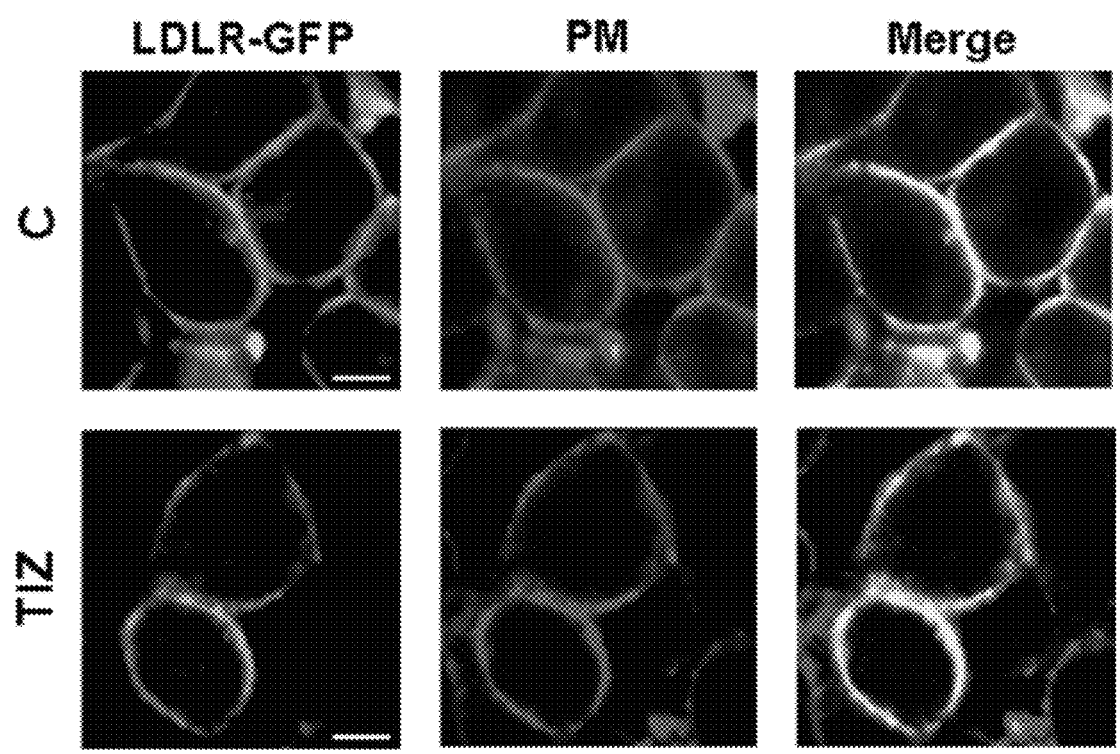
FIG. 11. Tizoxanide does not influence human low-density lipoprotein receptor (LDLR) plasma membrane targeting. MDCK cells were transiently transfected with green fluorescent protein (GFP)-tagged internalization-defective human low-density lipoprotein receptor mutant (LDLR-A18-GFP plasmid) (40) and, after 8 h, treated with TIZ (10 µg/ml) or vehicle for the following 16 h. After blocking protein synthesis with cycloheximide for 1 h, plasma membranes were stained using CellMask™ Orange plasma membrane (PM) stain, and imaged using a Leica DM-IL fluorescence microscope equipped with UV excitation filters. The images were captured with a Leica DC-300 camera using Leica Image-Manager500 software. Levels of LDLR-GFP (green) and PM (red) were detected in untreated (upper panels) or TIZ treated (bottom panels) transfected MDCK cells. The overlay of the two fluorochromes is shown (merge). Sections of the same images (bar=10 µm) of a representative experiment are shown.

Antiviral activity of thiazolides against different strains of influenza A virus. The effect of thiazolide treatment was investigated in human and canine cells after infection with four different strains of influenza A virus: the mammalian H1N1 A/PR/8/34 (PR8) and A/WSN/33 (WSN), and H3N2 A/Firenze/7/03 (A/FI) viruses, and the H5N9 low-pathogenicity avian strain A/Ck/It/9097/97 (A/Ck). Madin-Darby canine kidney (MDCK) cells infected with PR8, WSN or A/Ck influenza viruses were treated with different concentrations of NTZ, TIZ or vehicle immediately after the virus adsorption period, and virus yield was determined at 24 h post-infection (p.i.). NTZ treatment caused a dose-dependent inhibition of virus replication with an EC50 of 1, 0.5 and 1 µg/ml for PR8, WSN and A/Ck viruses respectively (FIG. 1B). TIZ was equally active against all influenza A strains with an EC50 of 1 µg/ml (PR8) and 0.5 µg/ml (WSN and A/Ck) (FIG. 1B). TIZ was also very effective in inhibiting the replication of H3N2 A/FI influenza A and B/Parma/3/04 influenza B viruses (FIGS. 10 and 11). Neither NTZ nor TIZ were cytotoxic at the effective antiviral concentration for uninfected cells (CC50>50 µg/ml). In addition to canine MDCK cells typically used for influenza virus studies, TIZ was effective in inhibiting influenza A virus replication at submicromolar (EC50=0.3 µg/ml) non-toxic concentrations in different types of human cells, including monocytic U937, T-lymphocytic Jurkat and alveolar type II-like A549 cells (FIG. 1C). The anti-influenza activity of TIZ was independent of the m.o.i. of infection, and a dramatic block of H1N1 PR8 virus replication was equally detected under conditions of multi- and single-step virus growth (FIG. 10 C,D). The antiviral activity of several thiazolides against PR8 influenza A virus is collected in Table 1. Among the thiazolides tested, NTZ (1), TIZ (2), tizoxanide sodium salt (3), compounds 14-16, 27, 28, 36 and 37 were found to be potent and selective. Compounds 27 and 28 were highly selective and were 10 times more potent than NTZ and TIZ, each with EC50=0.1 µg/ml and CC50>50 µg/ml.

Table 1 presents data from the influenza A cell assay for thiazolides.

TABLE 1

Influenza A Cell Assay Results (PR8, MDCK cells).

| | Virus Yield | | Toxicity | |
|---|---|---|---|---|
| No. | $EC_{50}$ µg/ml | $EC_{90}$ µg/ml | $LD_{50\,(MTT)}$ µg/ml | S.I. $LD_{50}/EC_{50}$ |
| 1 | 1 | 7 | >50 | >50 |
| 2 | 1 | 9 | >50 | >50 |
| 3 | 0.4 | 2.5 | >50 | >125 |
| 14 | 1 | 8 | 20 | 20 |
| 15 | 1 | 7 | 30 | 30 |
| 16 | 1 | 8 | 20 | 20 |
| 17 | 3 | 9 | >50 | >16.7 |
| 27 | 0.1 | 0.8 | >50 | >500 |
| 28 | 0.1 | 0.7 | >50 | >500 |
| 29 | 10 | >50 | >50 | >5 |
| 30 | 10 | >50 | >50 | >5 |
| 31 | >50 | >50 | >50 | ND |
| 32 | >50 | >50 | >50 | ND |
| 33 | >50 | >50 | >50 | ND |
| 34 | >50 | >50 | >50 | ND |
| 35 | >50 | >50 | >50 | ND |
| 36 | 1 | 8 | >50 | >50 |
| 37 | 0.6 | 15 | >50 | >83.3 |
| 38 | 25 | >50 | >50 | >2 |
| 39 | 10 | 30 | >50 | >5 |
| 51 | 3.5 | 9 | 30 | 9 |
| 52 | 30 | >50 | >50 | >1.6 |
| 53 | 10 | >50 | >50 | >5 |
| 54 | 10 | >50 | >50 | >5 |
| 59 | 5 | 30 | >50 | >10 |
| 63 | 10 | >50 | >50 | >5 |
| 64 | >50 | >50 | >50 | ND |
| 65 | >50 | >50 | >50 | ND |
| 66 | >50 | >50 | >50 | ND |

Thiazolides act at a post-entry level. To investigate whether thiazolide-treatment before virus adsorption could protect host cells from viral infection, MDCK cells were treated with 10 µg/ml TIZ for 12, 6 or 3 h. At the indicated times the drug was removed, and cell monolayers were washed three times before infection with PR8 virus. As shown in FIG. 1D (pre), tizoxanide (2) pre-treatment of cells up to 12 h before viral infection had no effect on influenza virus replication. Moreover, treatment of the viral inoculum (data not shown) or treatment of cells only during the adsorption period did not inhibit virus replication (FIG. 1D), indicating that the drug is not directly affecting virus infectivity, nor its binding or entry into target cells. TIZ treatment initiated between 0 and 3 h p.i. was the most effective in inhibiting virus replication (FIG. 1D, post). Treatment started at 6 h p.i. was less effective, but still able to inhibit virus replication, whereas the drug was ineffective when administered at 12 h p.i. A single administration of the drug after virus adsorption was effective in inhibiting virus replication for at least 48 h after infection (FIG. 1E).

Thiazolides selectively alter viral hemagglutinin maturation. To investigate whether the anti-influenza activity of thiazolides was caused by protein synthesis alterations, mockinfected or PR8-infected cells treated with TIZ soon after virus adsorption were labeled with [35S]-methionine-cysteine ([35S]-Met/Cys) at different times p.i., and proteins were analyzed by SDS/PAGE and autoradiography, or Western blot analysis. As shown in FIG. 2A, TIZ did not inhibit host protein synthesis (bottom), nor cause detectable alterations in the electrophoretic pattern of the synthesized polypeptides (top); in addition, TIZ did not affect phosphorylation of eukaryotic initiation factor 2α (eIF2-α) (middle) in either uninfected or PR8-infected cells. The main influenza virus proteins were found to be synthesized in large amounts in untreated cells starting at 4 h p.i.; no major changes in influenza virus protein synthesis were detected in treated cells, with the exception of the disappearance of a band of approximately 79 kDa mol·wt., subsequently identified as the mature isoform of the hemagglutinin precursor, and the simultaneous appearance of a faster-migrating band of 74 kDa (FIG. 2A).

To determine whether TIZ-treatment selectively alters HA synthesis, mock-infected or PR8-infected MDCK cells treated with TIZ (10 µg/ml) were metabolically labeled at 5 h p.i. (4 h-pulse), and radiolabeled proteins were immunoprecipitated with anti-hemagglutinin monoclonal antibodies and then processed for SDS-PAGE and autoradiography. Data shown in FIG. 2B identify the protein whose electrophoretic mobility is altered by TIZ as the viral HA0 precursor. To determine whether the TIZ-induced HA0 modification was transient, mock-infected or PR8-infected MDCK cells treated with TIZ (10 µg/ml) or the N-glycosylation inhibitor tunicamycin (TM, 5 µg/ml) were metabolically labeled at 3 h p.i. for the next 15 h, and proteins were analyzed by SDS/PAGE and autoradiography. Alternatively, PR8-infected cells were labeled at 5 h p.i. and then chased in the presence of 10 mM cold methionine and 1 mM cycloheximide for the next 3 h p.i. As shown in FIG. 2C, TIZ-induced HA0 posttranslational modification was still evident at 18 h p.i., and appeared to differ from TM-induced alteration, as indicated by a different electrophoretic mobility pattern of the two HA0 forms; in addition, whereas TM caused a decrease in HA0 accumulation, as previously described, prolonged TIZ-treatment did not reduce intracellular HA0 levels in infected cells. Differently from TM, TIZ did not induce the expression of the glucose-regulated stress protein Grp78/BiP, a marker of the unfolded protein response, in MDCK cells (FIG. 2C). Results from the chase experiment indicated that in untreated cells HA0 reached the mature 79 kDa form between 10 and 20 min after synthesis, whereas in the presence of TIZ the slower-migrating 74 kDa HA0 form started to appear later (30 min) after synthesis (FIG. 2D), and no further change in electrophoretic mobility was detectable in the next 2.5 hours (data not shown).

To determine whether TIZ is inhibiting HA0 glycosylation, PR8-infected cells were treated with TIZ or tunicamycin after virus adsorption and, at 6 h p.i., were labeled with either [35S]-Met/Cys, [3H]-glucosamine or [3H]-mannose. As shown in FIG. 3A, whereas TM completely prevented HA0 glycosylation, treatment with TIZ did not decrease glucosamine and actually increased mannose incorporation into the immature HA0 form. However, the thiazolide appears to act differently from the inhibitors of α-mannosidase I, 1-deoxymannojirimicin, and α-mannosidase II, swainsonine, as indicated by the different electrophoretic mobility of TIZ-induced immature HA0 as compared to the HA0 forms present in cells treated with the two inhibitors (FIG. 3B).

Figure 3:
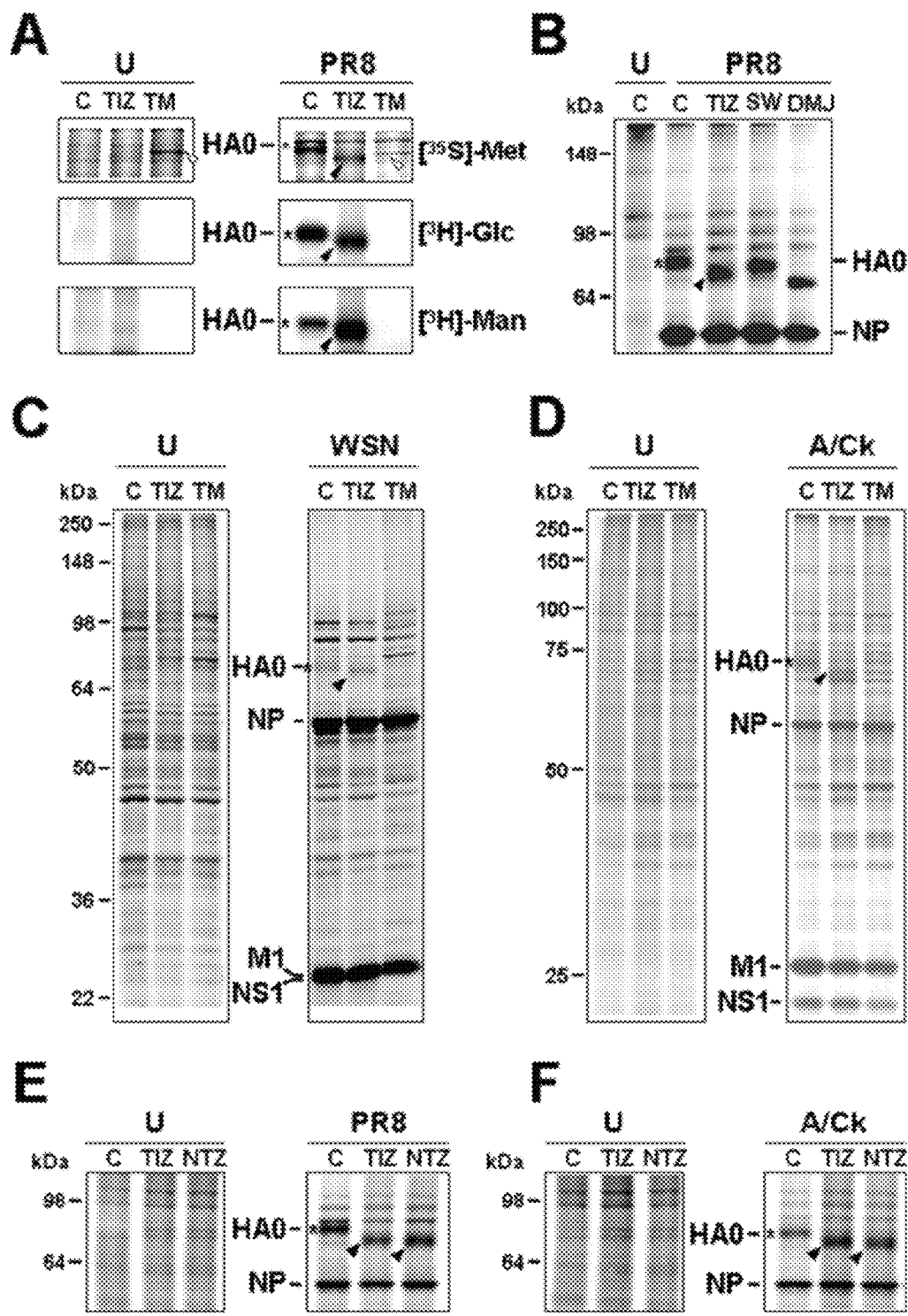
FIG. 3. Thiazolides interfere with viral hemagglutinin N-glycosylation. A, mock-infected (U) or PR8-infected (PR8) MDCK cells were treated with 10 μg/ml TIZ, 5 μg/ml TM or vehicle (C) after virus adsorption. At 6 h p.i., cells were labeled for 4 h with [35S]-Met/Cys (top), [3H]-glucosamine (middle) or [3H]-mannose (bottom). Radiolabeled samples were processed for SDS-PAGE and autoradiography. Sections of fluorograms from SDS/PAGE gels are shown. White arrows indicate TM-induced Grp78/BiP. B, mock-infected (U) or PR8-infected MDCK cells were treated with 10 μg/ml TIZ, 10 μg/ml swainsonine (SW), 15 μg/ml 1-deoxymannojirimicin (DMJ) or vehicle (C) after virus adsorption. At 6 h p.i., cells were labeled with [35S]-Met/Cys (4 h-pulse), and radiolabeled samples were processed for SDS-PAGE and autoradiography. C-D, autoradiography of radiolabeled proteins from mock-infected (U) or WSN-infected (WSN) A549 cells (C), and mock-infected or avian influenza A virus-infected (A/Ck) MDCK cells (D) treated with 5 μg/ml TIZ, 5 μg/mltunicamycin (TM) or vehicle (C) after virus adsorption. At 3 h (WSN) or 6 h (A/Ck) p.i., cells were labeled with [35S]-Met/Cys for 15 h (WSN) or 4 h (A/Ck). E-F, autoradiography of radiolabeled proteins from mock-infected (U) PR8-infected (PR8) (E) or avian influenza A virus-infected (A/Ck) (F) MDCK cells treated with 10 μg/ml TIZ, 10 μg/ml nitazoxanide (NTZ) or vehicle (C) after virus adsorption. At 6 h p.i., cells were labeled with [35S]-Met/Cys for 4 h. A-F, viral proteins HA0, NP, M1 and NS1 are indicated. The slower- and faster-migrating HA0 forms in untreated or thiazolide-treated cells are identified by asterisk and triangle respectively.

It is known that HA maturation is influenced both by the host cell glycosylation machinery and the virus strain. To determine whether the described HA0 alteration was specific for PR8 virus or was cell-dependent, human lung epithelial A549 cells were infected with the influenza A human WSN strain, whereas MDCK cells were infected with the avian A/Ck strain. In both cases, alterations in HA0 maturation analogous to the ones described for the PR8 strain were detected (FIGS. 3, C and D), indicating that TIZ is able to inhibit HA0 maturation, independently of the type of host cell and influenza A strain. Finally, as shown in FIGS. 3, E and F, nitazoxanide caused similar alterations in the hemagglutinin of human (E) and avian (F) influenza viruses.

Figure 4:
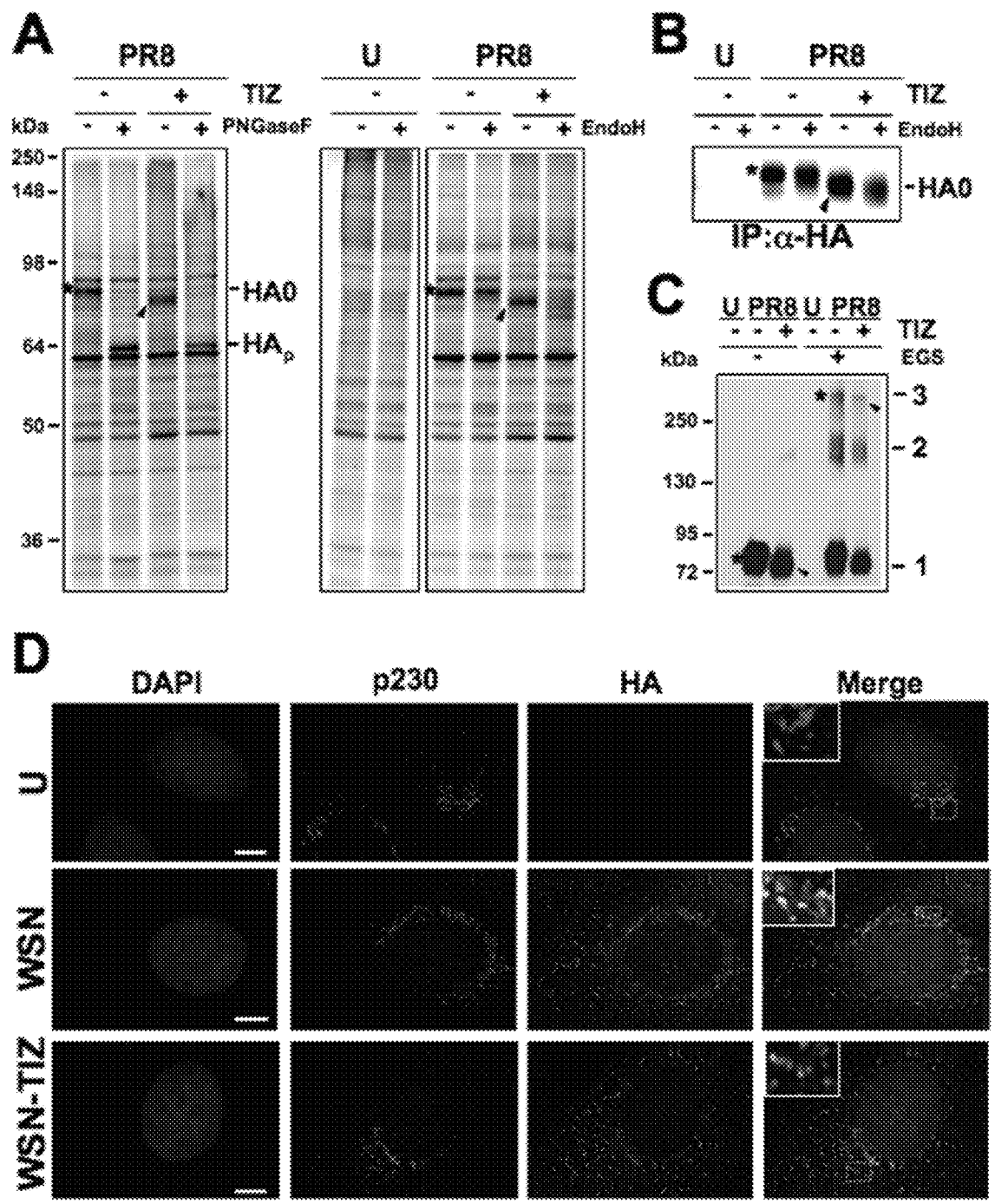
FIG. 4. Tizoxanide blocks HA maturation at an EndoH-sensitive stage. A, mock-infected (U) or PR8-infected (PR8) MDCK cells treated with 10 μg/ml TIZ (+) or vehicle (−) after virus adsorption were labeled with [35S]-Met/Cys (4 h-pulse) at 5 h p.i. Radiolabeled proteins were digested (+) or not (−) with PNGase-F or Endo-H, and processed for SDS-PAGE and autoradiography. Uncleaved glycosylated (HA0) and nonglycosylated (HAp) hemagglutinin precursor forms are indicated. B, MDCK cells treated as in A were labeled with [35S]-Met/Cys (4 h-pulse) at 6 h p.i. Radiolabeled proteins were immunoprecipitated with anti-HA antibodies (α-HA), digested (+) or not (−) with Endo-H, and processed for SDS-PAGE. Sections of fluorograms are shown. C, whole-cell extracts from mock-infected (U) and PR8-infected (PR8) MDCK cells treated with TIZ (+) or vehicle (−) were incubated with (+) or without (−) the crosslinking reagent EGS (0.2 mM) and processed for Western blot using anti-HA antibodies. HA monomers (1), dimers (2) and trimers (3) are indicated. A-C, slower- and faster-migrating HA0 forms in untreated or TIZ-treated cells are identified by asterisk and triangle respectively. D, immunofluorescence of mock-infected (U) and WSN-infected A549 cells treated with TIZ (5 μg/ml) or vehicle for 24 h, labeled with anti-p230 trans-Golgi (red) and anti-HA (green) antibodies. Nuclei are stained with DAPI (blue). The overlay of the three fluorochromes is shown (merge). The enlarged areas (insets) highlight the localization of HA in untreated and TIZ-treated cells. Images were captured and deconvolved with a DeltaVision microscope using SoftWoRx-2.50 software. Bar=5 μm.

Tizoxanide inhibits HA transport to the cell membrane and prevents virus exit from host cells. Glycosylation of HA, like other cell surface glycoproteins, is initiated in the ER, adding the "high mannose" oligosaccharides. The mannose-rich sugar component is processed in the Golgi apparatus during the transport to the cell surface, and terminal glycosylation occurs in trans cisternae of the Golgi apparatus. To investigate whether TIZ could affect HA0 passage through the Golgi, we subjected aliquots of radiolabeled proteins and HA0 immunoprecipitated samples to digestion with endo-β-N-acetylglucosaminidase H (Endo-H), an enzyme that removes N-linked carbohydrate chains that have not been terminally glycosylated or with peptide N-glycosidase F (PNGase-F), an enzyme that removes all N-glycans. As expected, both forms of the protein were sensitive to PNGase-F digestion; however, whereas HA0 from control cells was terminally glysosylated becoming Endo-H resistant, HA0 from TIZ-treated cells remained sensitive to digestion with the protease up to 4 h after synthesis (FIGS. 4, A and B). As shown in FIG. 4C, the TIZ-induced alterations did not prevent HA0 ability to form trimers.

Since acquisition of Endo-H resistance is a marker for transport into the cis and middle Golgi compartments, these results indicate that the TIZ-induced alteration may block HA0 trafficking between the ER and the Golgi complex, preventing its transport to the plasma membrane. Inhibition of transport to the trans-Golgi compartment was in fact detected by immunofluorescence using specific trans-Golgi antibodies (FIG. 4D). To confirm that TIZ-treatment inhibited HA transport to the host-cell plasma membrane preventing the exit of mature viral particles, mock-infected and PR8-infected MDCK cells were treated with TIZ (10 µg/ml) or tunicamycin (5 µg/ml) after virus adsorption and levels of cytoplasmic (FIG. 5A) and plasma membrane (FIG. 5B) viral hemagglutinin were detected by immunofluorescence at 16 h p.i. These studies confirmed that, whereas HA0 cytoplasmic levels in TIZ-treated cells were similar to control (FIG. 5A), plasma membrane levels of the viral protein were dramatically decreased in TIZ-treated cells (FIG. 5B, top). A substantial decrease in HA plasma membrane levels after TIZ treatment was further confirmed by determining the biological function of plasma membrane-incorporated HA by receptor-binding (hemadsorption of erythrocytes) assay (FIG. 5B, bottom). In parallel studies, after transient transfection of MDCK cells with a GFP-tagged internalization-defective human low-density lipoprotein receptor mutant (LDLR-A18-GFP plasmid), it was found that TIZ did not inhibit plasma membrane targeting of LDLR, suggesting a selective effect of thiazolides (FIG. 11). Similar results were obtained after transient transfection of MDCK cells and HEK-293 cells with a different plasma membrane cellular glycoprotein, the human Toll-like receptor-4 (data not shown).

In parallel samples, mock-infected and PR8-infected cells were metabolically labelled with [35S]-Met/Cys at 3 h p.i. for the next 21 h, and radiolabeled virions were purified from the supernatant of infected cells. Proteins incorporated into viral particles were analyzed by SDS-PAGE and autoradiography. As shown in FIG. 5C, viral proteins could not be detected in the supernatant of TIZ-treated cells. The dramatic reduction of viral particles was confirmed by determining virus yields from parallel, non-labeled samples by TCID50 infectivity assay (FIG. 5D, top) or HAU assay (FIG. 5D, bottom) at 24 h p.i.

Combination studies with nitazoxanide and neuraminidase inhibitors zanamivir and oseltamivir against PR8 influenza A virus demonstrate synergistic activity. In order to determine the antiviral activity of NTZ in combination with clinical influenza inhibitors, we tested combinations of NTZ with zanamivir and combinations of NTZ with oseltamivir at different concentrations. Zanamivir and oseltamivir are neuraminidase (NA) inhibitors that impair the efficient release of viruses from the infected host cell and act by a mechanism distinctly different from that of the thiazolides.

The effect of NTZ and zanamivir combination treatment was investigated in canine cells after infection with mammalian H1N1 A/PR/8/34 (PR8) virus. Madin-Darby canine kidney (MDCK) cells infected with PR8 influenza viruses were treated with different concentrations of NTZ, zanamivir, or vehicle immediately after the virus adsorption period, and virus yield was determined at 24 h post-infection (p.i.).

Figure 6:
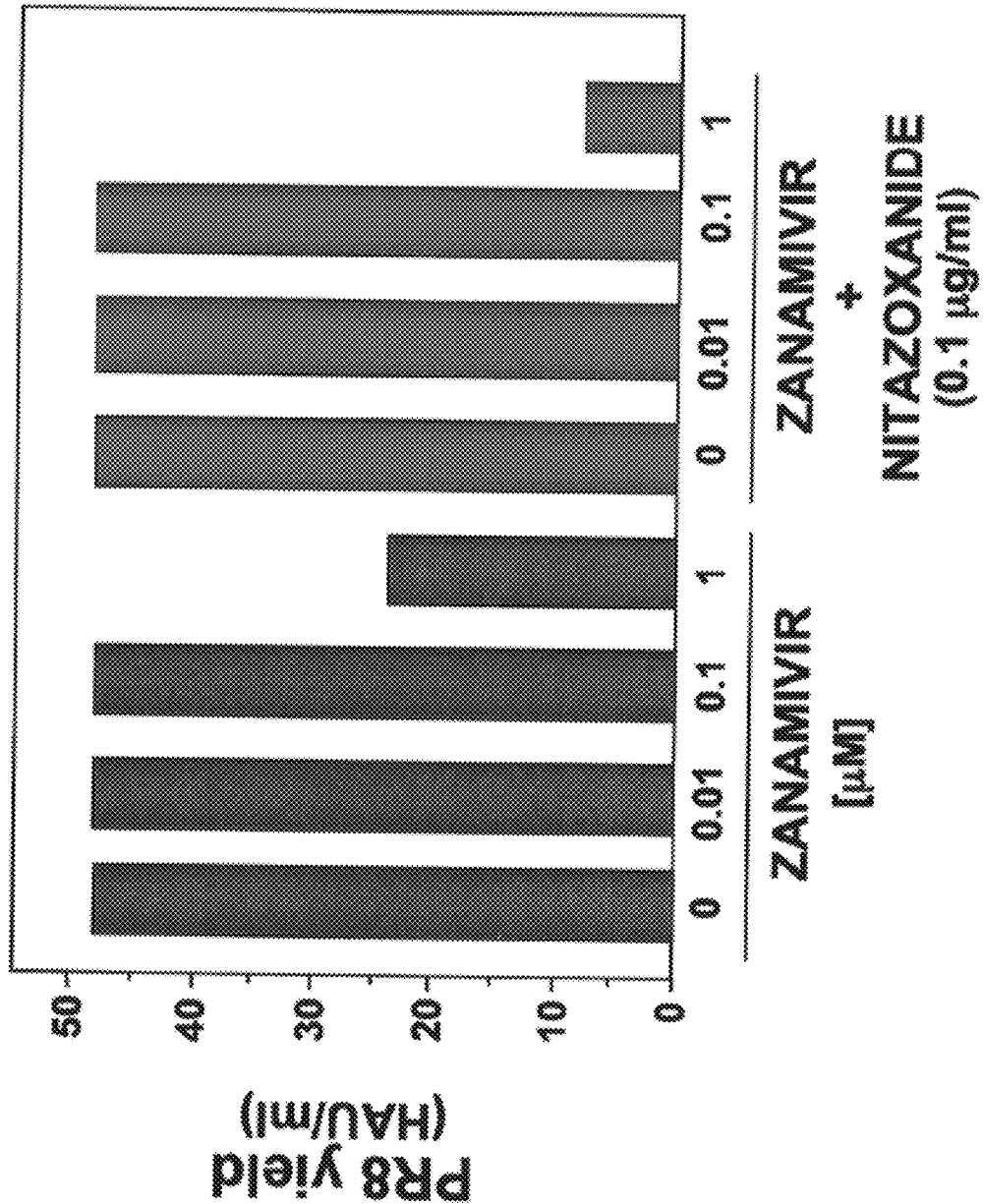
FIG. 6 Antiviral activity of Zanamivir at three concentrations and Zanamivir combined with Nitazoxanide at 0.1 ug/mL against Influenza A. Zanamivir was tested alone against influenza A (MDCK/PR8) at doses of 0.01, 0.1 and 1.0 µM and in the presence of NTZ at 0.1 µg/ml.
Figure 7:
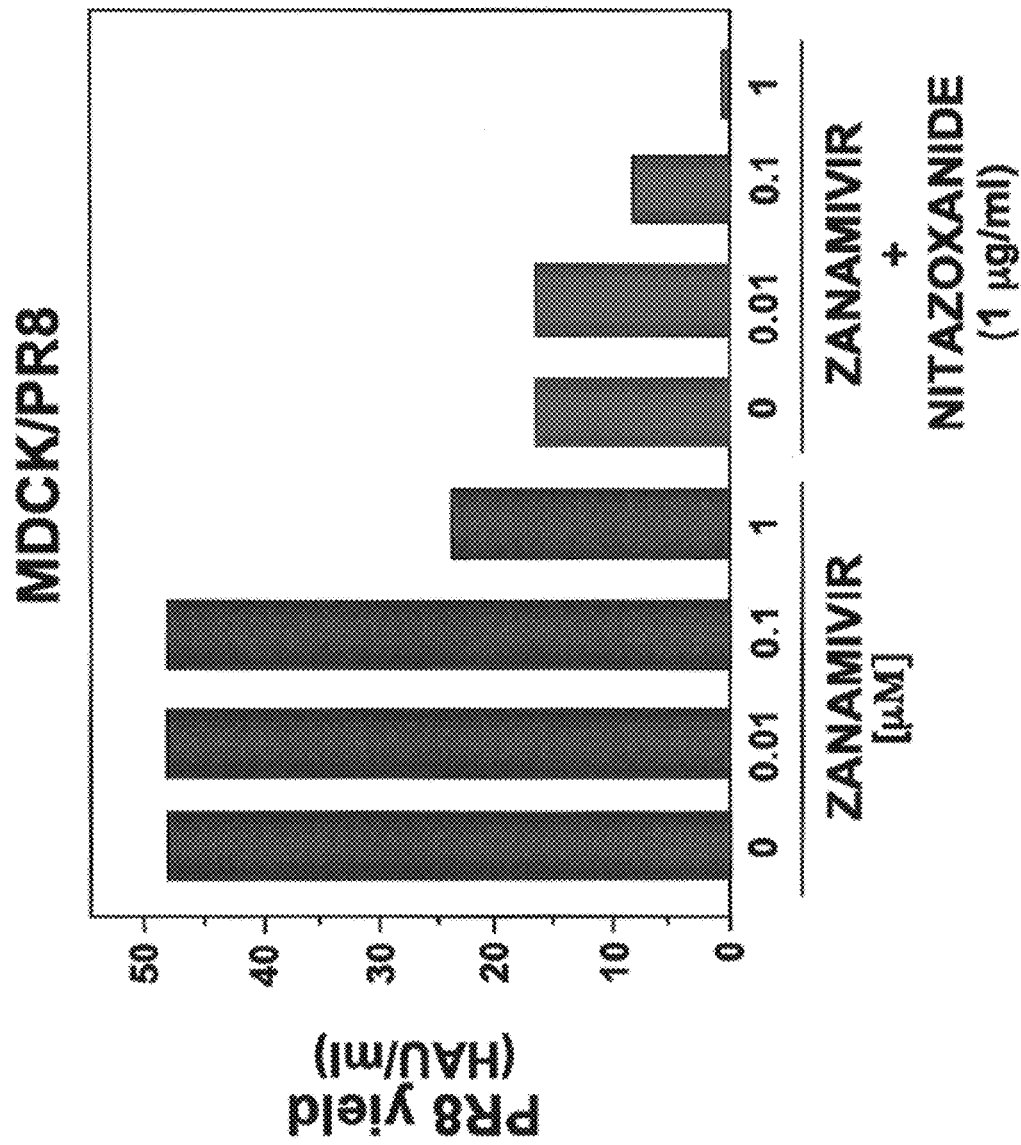
FIG. 7 Antiviral activity of Zanamivir at three concentrations and Zanamivir combined with Nitazoxanide at 1.0 ug/mL against Influenza A. Zanamivir was tested alone against influenza A (MDCK/PR8) at doses of 0.01, 0.1 and 1.0 µM and in the presence of NTZ at 1.0 µg/ml.

In separate studies, NTZ treatment caused a dose-dependent inhibition of virus replication with an EC50 of 1 µg/ml (3.3 □M) for PR8 virus (FIG. 1B). Table 2 below summarizes the antiviral data from the combination experiments. Activity is expressed as reduction of HAU/ml relative to untreated control. In the experiments with zanamivir, NTZ appeared to be slightly more potent than in the previous study, and had EC50 of ~0.66 µg/ml (~2.2 µM) Zanamivir alone gave 50% reduction (inhibition) of virus yield only at the highest test concentration of 1 therefore we determined that zanamivir had an EC50 of 1 µM under these experimental conditions (FIGS. 6 and 7, left side). A combination of zanamivir at 1 µM with NTZ at 0.1 µg/ml (0.33 µM) resulted in 83% reduction of viral replication relative to untreated control, and corresponds to an approximately 3-fold potency increase relative to treatment with zanamivir alone (FIG. 6, right side).

TABLE 2

| Anti-Influenza Activity of NTZ and Zanamivir Combinations PR8 Yield: HAU/ml | | | | |
|---|---|---|---|---|
| Nitazoxanide | | Zanamivir (µM) | | |
| (µg/ml) | Control | 0.01 | 0.1 | 1 |
| 0 | 48 | 48 | 48 | 24 |
| 0.1 | 48 | 48 | 48 | 8 |
| 1 | 16 | 16 | 8 | 1 |

Treatment with zanamivir alone at 0.1 µM had no effect on viral replication (FIG. 7, left side). However, a combination of zanamivir at 0.1 µM and NTZ at 1.0 µg/ml (3.3 µM) resulted in 50% greater reduction of viral replication relative to treatment with NTZ alone (FIG. 7, right side). These results correspond to an approximately 6-fold potency increase relative to treatment with zanamivir alone and a 2-fold potency increase relative to treatment with NTZ alone. A combination of zanamivir at 1.0 µM and NTZ at 1.0 µg/ml (3.3 µM) resulted in 94% reduction of viral replication relative to treatment with NTZ alone (FIG. 7, right side). These results correspond to an approximately 24-fold potency increase relative to treatment with zanamivir alone and a 16-fold potency increase relative to treatment with NTZ alone. Taken together, these results suggest that the antiviral activity of zanamivir and NTZ combinations are synergistic against the PR8 influenza A virus.

In a similar fashion, the effect of NTZ and oseltamivir combination treatment was investigated in canine cells after infection with mammalian H1N1 A/PR/8/34 (PR8) virus. Madin-Darby canine kidney (MDCK) cells infected with PR8 influenza viruses were treated with different concentrations of NTZ, oseltamivir, or vehicle immediately after the virus adsorption period, and virus yield was determined at 24 h post-infection (p.i.).

Figure 8:
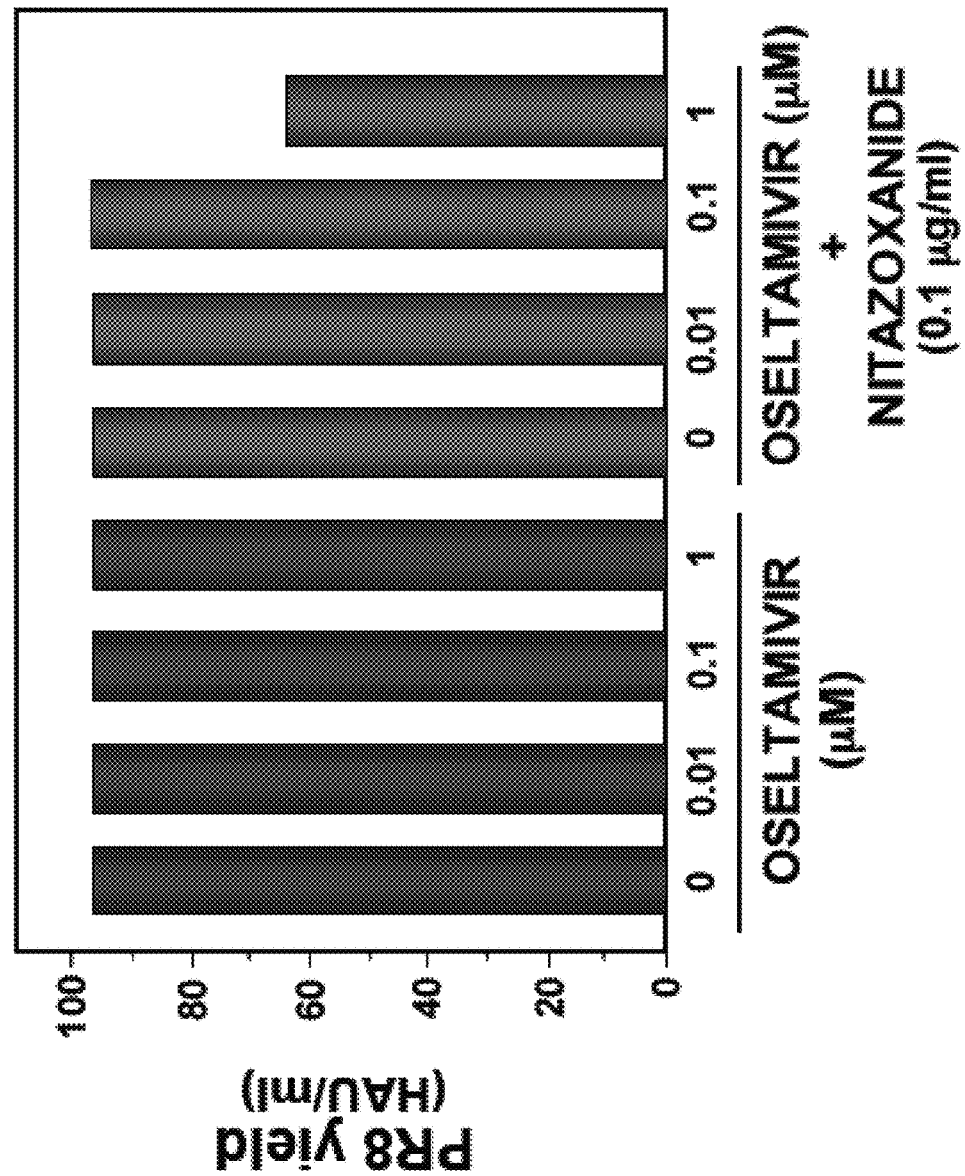
FIG. 8 Antiviral activity of Oseltamivir at three concentrations and Oseltamivir combined with Nitazoxanide at 0.1 ug/mL against Influenza A. Oseltamivir was tested alone against influenza A (MDCK/PR8) at doses of 0.01, 0.1 and 1.0 µM and in the presence of NTZ at 0.1 µg/ml.
Figure 9:
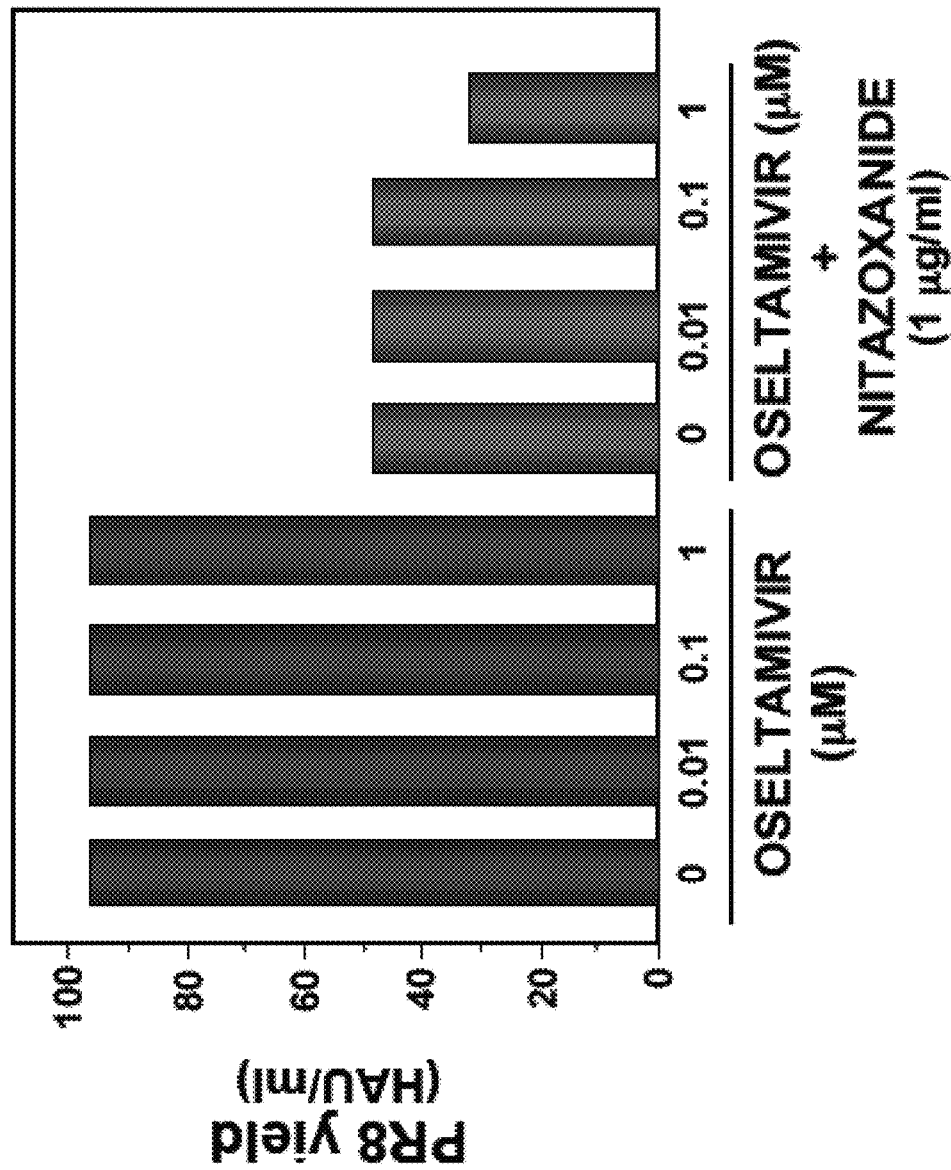
FIG. 9 Antiviral activity of Oseltamivir at three concentrations and Oseltamivir combined with Nitazoxanide at 1.0 ug/mL against Influenza A. Oseltamivir was tested alone against influenza A (MDCK/PR8) at doses of 0.01, 0.1 and 1.0 □M and in the presence of NTZ at 1.0 µg/ml.

In these experiments, NTZ demonstrated an EC50 of 1 µg/ml (3.3 We did not observe reduction (inhibition) of virus yield with oseltamivir alone at test concentrations up to 1 µM, therefore the EC50 was not determined for oseltamivir (FIGS. 8 and 9, left side). A combination of oseltamivir at 1 µM with NTZ at 0.1 µg/ml (0.33 µM) resulted in 33% increased reduction of viral replication, corresponding to an approximately 1.5-fold potency increase relative to treatment with oseltamivir or NTZ alone (FIG. 8, right side). Note that the NTZ dose was one-tenth of its established EC50.

A combination of oseltamivir at 1.0 µM and NTZ at 1.0 µg/ml (3.3 µM) resulted in 67% increased reduction of viral replication relative to treatment with oseltamivir alone and 33% increased reduction of viral replication relative to treatment with NTZ alone (FIG. 9, right side). These results correspond to an approximately 3-fold potency increase relative to treatment with oseltamivir alone and a 1.5-fold potency increase relative to treatment with NTZ alone. Taken together, these results suggest the antiviral activity of oseltamivir and NTZ combinations are somewhere between additive and synergistic against the PR8 influenza A virus.

Results from several biochemical approaches demonstrate that TIZ blocks HA terminal glycosylation at a stage preceding resistance to endoglycosidase-H digestion, which is a marker for transport into the cis and middle Golgi compartments. Immunomicroscopy studies and analysis of viral particles produced by infected cells confirm that the TIZ-induced alterations impair HA0 trafficking between the ER and the Golgi complex, preventing its transport and insertion into the host cell plasma membrane, and blocking the exit of mature virions from host cells. Whether the alteration of HA maturation is caused by direct binding of TIZ to the viral glycoprotein or is due to a cell-mediated effect remains to be established.

Thiazolides have previously been shown to possess antiviral activity against two different RNA viruses, hepatitis C (HCV), a positive strand RNA virus, and rotavirus, a double-strand RNA virus, and a DNA virus, the hepatitis B (HBV) virus. The wide-spectrum antiviral activity suggests a cell-mediated effect rather than a specific viral target. The possibility that maturation of viral glycoproteins may be involved in the antiviral activity against HBV and HCV is currently under study. In the case of rotavirus, TIZ-induced modification of the structural viral glycoprotein VP7 has been recently shown (Santoro M G and Rossignol J F, unpublished results), reinforcing the hypothesis that maturation and transport of key viral glycoproteins could be a general mechanism of the antiviral activity of this new class of drugs. The finding that thiazolides do not significantly affect the replication of human rhinovirus, a picornavirus whose maturation does not require viral glycoprotein trafficking to the cell membrane, further supports this hypothesis.

The abbreviations used are: NTZ, nitazoxanide; TIZ, tizoxanide; EC50, effective concentration 50%; CC50, cytotoxic concentration 50%; HA, hemagglutinin; TM, tunicamycin; Endo-H, endo-β-Nacetylglucosaminidase H; PNG-ase F, peptide N-glycosidase F; TCID50, tissue culture infective dose 50%; SW, swainsonine; DMJ, 1-deoxymannojirimicin; HAU/ml, hemagglutinating units/ml, EGS, ethylene glycol bis(succinimidylsuccinate).

Low dose administration of thiazolides such as NTZ to treat virus infection. NTZ can be administered orally at a dose of 300 mg or 600 mg twice daily for 5 days as a treatment of influenza. Clinical trials have shown that this dosage regimen has the ability to treat influenza. Preferably, the dosage of nitazoxanide is 300 mg twice daily for 5 days, which is less than the dosage of NTZ needed to treat intestinal infections, thereby enabling a reduction of side effects associated with higher dosages. Thiazolides can also be administered as a modified release bi-layer tablet. As such, thiazolides can be administered in 100 mg, 200 mg, 300 mg, 400 mg, 500 mg or 600 mg doses twice daily for 5 days to treat virus infection.

Thiazolides such as nitazoxanide have also been found to have activity against other respiratory viruses. In vivo data is presented in Table 3.

TABLE 3

| Activity Against Other Respiratory Viruses | | |
|---|---|---|
| Virus | $EC_{50}$ (µg/mL) | $CC_{50}$ (µg/mL) |
| Parainfluenza | 0.5 | >50 |
| Coronavirus | 1.0 | >50 |
| Adenovirus | 0.2 | >50 |
| Respiratory syncytial virus | 0.5 | >50 |
| Rhinovirus | >10 | >50 |

Interestingly, thiazolides such as NTZ also have the ability to treat patients with influenza-like illness (MI). Influenza-like illness present symptoms of influenza, which may be caused by another virus or pathogen.

Evaluation of the effect of twice daily nitazoxanide for 5 days on the duration of symptoms in pediatric patients and adults with influenza-like illnesses was conducted. Two double-blind placebo controlled trials were conducted. Children 12 months-11 years of age were given NTZ suspension (n=100, 50 per group) and Patients ≥12 years of age were given NTZ 500 mg tablets (n=86, 43 per group). Single center trials were conducted. Studies were based on TAMIFLU® trials. The trials followed specific Inclusion/exclusion criteria. Inclusion required children age 1-11 years of patients ≥12 years of age with a fever >100° F. with ≥1 respiratory symptom (including cough, nasal discharge, sneezing, sore throat, etc.) and/or with ≥1 constitutional symptom (myalgia, malaise, fatigue, headache, chills/sweat, etc.). Major exclusions included symptom duration >72 hours, pregnancy or breastfeeding, concurrent antibiotics/antiviral medication, or a history of asthma or other pulmonary disease.

Patients were randomized to receive NTZ or placebo b.i.d. for 5 days. Nasopharyngeal swab collected at baseline for rapid direct immunofluorescence assay (SimulFluor respiratory Screen) for 7 viruses (RSV, Influenza A & B, Parainfluenza 1-3, and Adenovirus). Symptoms recorded in a daily diary by the patient (or parent) with each symptom graded on a scale of 0 to 3: absent, mild, moderate, severe. Tissue was stored in a ziplock plastic bag and collected daily by study personnel for weighing. A follow up physical examination was conducted on day 7. The primary endpoint was the time from baseline to each symptom returning to absent or mild (<2). Secondary endpoints include antibiotic use, day 7 respiratory symptoms, daily tissue/mucus weight.

Results from additional biochemical approaches demonstrate that nitazoxanide has an effect on additional respiratory viruses. See Table 4 for patient makeup and Table 5 for virus detection. Table 5 shows that most patients did not test positive for the presence of Adenovirus, RSV, Influenza A, Parainfluenza 1. However, FIGS. 12-15 show that NTZ has the ability to treat patients that have influenza like illness. These data surprisingly show that patients who exhibit symptoms of influenza, but do not test positive for Adenovirus, RSV, Influenza A, Parainfluenza 1 can be treated with thiazolides such as NTZ.

TABLE 4

| Patients | | | | |
|---|---|---|---|---|
| | Children (<12 years of age) | | Adults (≥12 years of age) | |
| | NTZ | Placebo | NTZ | Placebo |
| Gender (M/F) | 24/26 | 29 | 10/33 | 17/26 |
| Age, Yrs (Mean ± S.D.) | 4.0 ± 2.8 | 3.5 ± 2.3 | 28.9 ± 13.3 | 31.4 ± 12.7 |
| Age, yrs (range) | 1-9 | 1-11 | 12-61 | 12-61 |
| Weight, kgs (Mean ± S.D) | 15.4 ± 6.0 | 14.8 ± 4.8 | 56.2 ± 11.2 | 58.9 ± 10.5 |
| Symptoms (%) | | | | |
| Nasal secretion | 100% | 100% | 100% | 98% |
| Nasal obstruction | 80% | 76% | 79% | 86% |
| Sneezing | 92% | 96% | 91% | 98% |
| Sore throat | 84% | 80% | 93% | 81% |
| Fever | 84% | 80% | 86% | 81% |
| Cough | 94% | 92% | 94% | 86% |
| Malaise | 92% | 88% | 91% | 88% |
| Headache | 70% | 66% | 70% | 79% |
| Chills | 60% | 50% | 65% | 60% |

TABLE 5

| Viruses Detected by Rapid Assay | | | | |
|---|---|---|---|---|
| | Children (<12 years of age) | | Adults (≥12 years of age) | |
| | NTZ | Placebo | NTZ | Placebo |
| Adenovirus (n, %) | 4 (8%) | 8 (16%) | 2 (5%) | 2 (5%) |
| RSV (n, %) | — | 1 (2%) | 1 (2%) | 3 (7%) |
| Influenza A (n, %) | 2 (4%) | — | 1 (2%) | — |
| Parainfluenza 1 (n, 5) | 1 (2%) | — | — | — |
| None (n, %) | 43 (86%) | 41 (82%) | 39 (91%) | 38 (88%) |

FIGURE LEGENDS

FIG. 1. Thiazolides inhibit influenza A virus replication acting at a post-entry level. A, structure of nitazoxanide (NTZ) and tizoxanide (TIZ). B, NTZ (blue circles) and TIZ (red circles) inhibit the replication of human (PR8, WSN) and avian (A/Ck) influenza A virus strains in MDCK cells. Virus yield was determined at 24 h p.i. C, antiviral activity of TIZ on influenza A PR8 virus in human monocytic U937 (●) and T-lymphoblastoid Jurkat (▲) cells, and WSN virus in human lung epithelial A549 cells (■). D, MDCK cells were treated with 10 µg/ml TIZ (filled bars) at the indicated times before infection (Pre), immediately after the adsorption period (Post), or only during the adsorption period (Ad, dashed bar). Empty bar represents untreated infected control (C). E, long-term antiviral activity of TIZ in PR8-infected MDCK cells treated with 10 µg/ml TIZ (filled circles) or vehicle (empty circles) after virus adsorption. B-E, virus yield, expressed in HAU/ml (B and E) or as percent of non-treated control (C and D), represents the mean±SD of duplicate samples from a representative experiment of three with similar results. *=P<0.01; **=P<0.05

Figure 2:
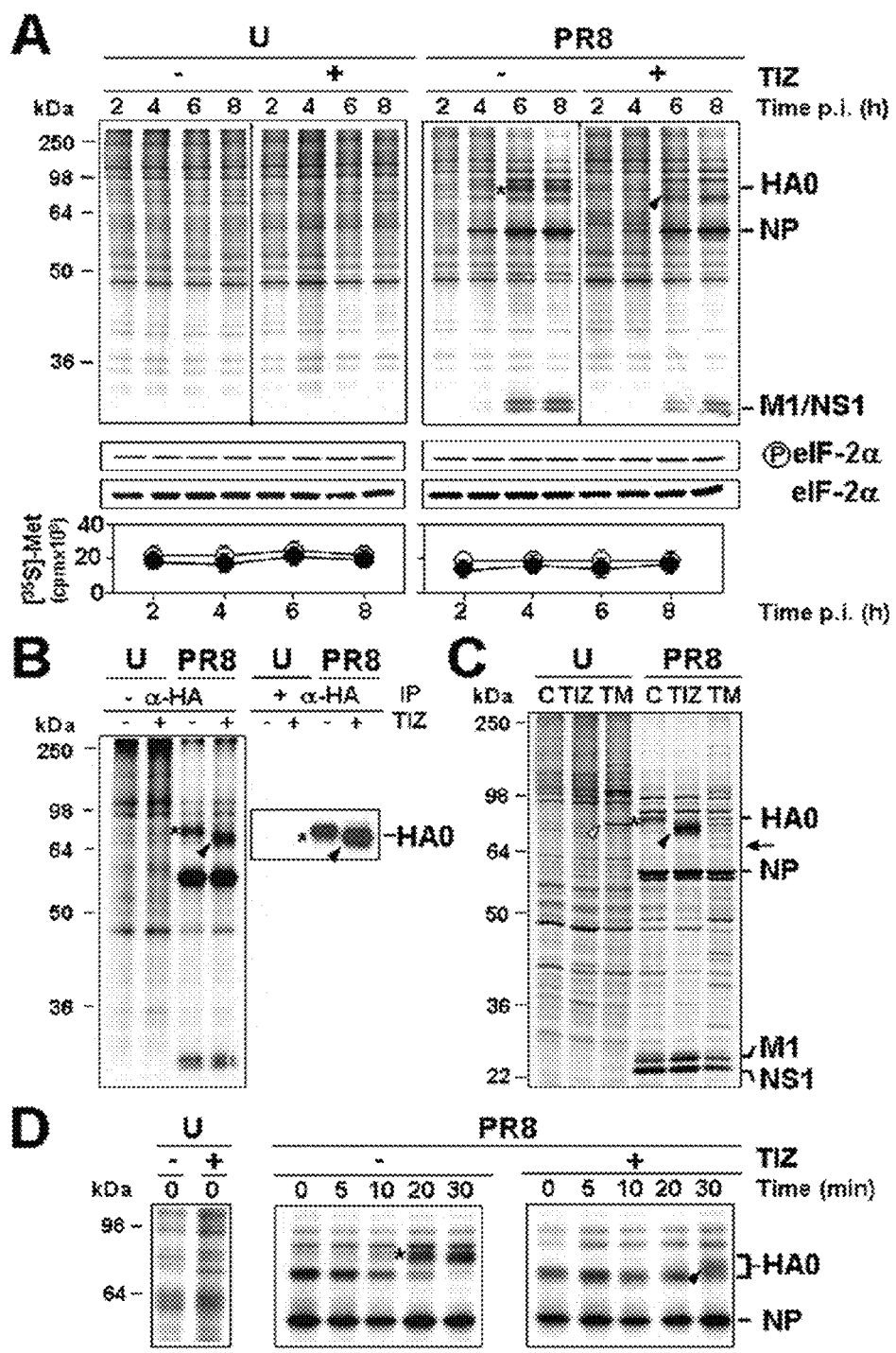
FIG. 2. Tizoxanide selectively alters influenza hemagglutinin maturation. A, effect of TIZ on the kinetics of PR8 virus protein synthesis. Autoradiography of [35S]-Met/Cys-labeled proteins (1.5 h-pulse) at different times p.i. from mock-infected (U) or PR8-infected cells treated with 10 μg/ml TIZ after virus adsorption (top). Viral proteins are indicated. In the same experiment, protein synthesis was determined by [35S]-Met/Cys-incorporation into proteins of cells treated with TIZ (●) or vehicle (○) (bottom), and phospho-eIF-2α protein levels were determined by immunoblot analysis using antiphosphoSer-51-eIF2α (p-eIF2α) or eIF2α panspecific antibodies (middle). B, hemagglutinin identification by immunoprecipitation with anti-HA antibodies after [35S]-Met/Cys-labeling at 5 h p.i. (4 h-pulse). Immunoprecipitated proteins (+αHA, IP) and radiolabeled proteins from the same samples before antibodies addition (−αHA) are shown. Positions of HA uncleaved precursor (HA0) is indicated. C, autoradiography of [35S]-Met/Cys-labeled proteins (15 h-pulse) from mock-infected (U) or PR8-infected cells treated with 10 μg/ml TIZ, 5 μg/ml tunicamycin (TM) or vehicle (C) after virus adsorption. White triangle and black arrow indicate TM-induced GRP78/BiP and nonglycosylated HA0 [identified by immunoblot (not shown)], respectively. D, autoradiography of [35S]-Met/Cys-labeled proteins (15 min-pulse at 5 h p.i., followed by chase for the indicated times) from PR8-infected cells treated as in A. A-D, the slower- and faster-migrating HA0 forms in untreated or TIZ-treated cells are identified by asterisk and black triangle respectively.

FIG. 2. Tizoxanide selectively alters influenza hemagglutinin maturation. A, effect of TIZ on the kinetics of PR8 virus protein synthesis. Autoradiography of [35S]-Met/Cys-labeled proteins (1.5 h-pulse) at different times p.i. from mock-infected (U) or PR8-infected cells treated with 10 µg/ml TIZ after virus adsorption (top). Viral proteins are indicated. In the same experiment, protein synthesis was determined by [35S]-Met/Cys-incorporation into proteins of cells treated with TIZ (●) or vehicle (○) (bottom), and phospho-eIF-2α protein levels were determined by immunoblot analysis using antiphosphoSer-51-eIF2α (p-eIF2α) or eIF2α panspecific antibodies (middle). B, hemagglutinin identification by immunoprecipitation with anti-HA antibodies after [35S]-Met/Cys-labeling at 5 h p.i. (4 h-pulse). Immunoprecipitated proteins (+αHA, IP) and radiolabeled proteins from the same samples before antibodies addition (−αHA) are shown. Positions of HA uncleaved precursor (HA0) is indicated. C, autoradiography of [35S]-Met/Cys-labeled proteins (15 h-pulse) from mock-infected (U) or PR8-infected cells treated with 10 µg/ml TIZ, 5 µg/ml tunicamycin (TM) or vehicle (C) after virus adsorption. White triangle and black arrow indicate TM-induced GRP78/BiP and nonglycosylated HA0 [identified by immunoblot (not shown)], respectively. D, autoradiography of [35S]-Met/Cys-labeled proteins (15 min-pulse at 5 h p.i., followed by chase for the indicated times) from PR8-infected cells treated as in A. A-D, the slower- and faster-migrating HA0 forms in untreated or TIZ-treated cells are identified by asterisk and black triangle respectively.

FIG. 3. Thiazolides interfere with viral hemagglutinin N-glycosylation. A, mock-infected (U) or PR8-infected (PR8) MDCK cells were treated with 10 µg/ml TIZ, 5 µg/ml TM or vehicle (C) after virus adsorption. At 6 h p.i., cells were labeled for 4 h with [35S]-Met/Cys (top), [3H]-glucosamine (middle) or [3H]-mannose (bottom). Radiolabeled samples were processed for SDS-PAGE and autoradiography. Sections of fluorograms from SDS/PAGE gels are shown. White arrows indicate TM-induced Grp78/BiP. B, mock-infected (U) or PR8-infected MDCK cells were treated with 10 µg/ml TIZ, 10 µg/ml swainsonine (SW), 15 µg/ml 1-deoxymannojirimicin (DMJ) or vehicle (C) after virus adsorption. At 6 h p.i., cells were labeled with [35S]-Met/Cys (4 h-pulse), and radiolabeled samples were processed for SDS-PAGE and autoradiography. C-D, autoradiography of radiolabeled proteins from mock-infected (U) or WSN-infected (WSN) A549 cells (C), and mock-infected or avian influenza A virus-infected (A/Ck) MDCK cells (D) treated with 5 µg/ml TIZ, 5 µg/ml tunicamycin (TM) or vehicle (C) after virus adsorption. At 3 h (WSN) or 6 h (A/Ck) p.i., cells were labeled with [35S]-Met/Cys for 15 h (WSN) or 4 h (A/Ck). E-F, autoradiography of radiolabeled proteins from mock-infected (U) PR8-infected (PR8) (E) or avian influenza A virus-infected (A/Ck) (F) MDCK cells treated with 10 µg/ml TIZ, 10 µg/ml nitazoxanide (NTZ) or vehicle (C) after virus adsorption. At 6 h p.i., cells were labeled with [35S]-Met/Cys for 4 h. A-F, viral proteins HA0, NP, M1 and NS1 are indicated. The slower- and faster-migrating HA0 forms in untreated or thiazolide-treated cells are identified by asterisk and triangle respectively.

FIG. 4. Tizoxanide blocks HA maturation at an EndoH-sensitive stage. A, mock-infected (U) or PR8-infected (PR8) MDCK cells treated with 10 μg/ml TIZ (+) or vehicle (−) after virus adsorption were labeled with [35S]-Met/Cys (4 h-pulse) at 5 h p.i. Radiolabeled proteins were digested (+) or not (−) with PNGase-F or Endo-H, and processed for SDS-PAGE and autoradiography. Uncleaved glycosylated (HA0) and nonglycosylated (HAp) hemagglutinin precursor forms are indicated. B, MDCK cells treated as in A were labeled with [35S]-Met/Cys (4 h-pulse) at 6 h p.i. Radiolabeled proteins were immunoprecipitated with anti-HA antibodies (α-HA), digested (+) or not (−) with Endo-H, and processed for SDS-PAGE. Sections of fluorograms are shown. C, whole-cell extracts from mock-infected (U) and PR8-infected (PR8) MDCK cells treated with TIZ (+) or vehicle (−) were incubated with (+) or without (−) the crosslinking reagent EGS (0.2 mM) and processed for Western blot using anti-HA antibodies. HA monomers (1), dimers (2) and trimers (3) are indicated. A-C, slower- and faster-migrating HA0 forms in untreated or TIZ-treated cells are identified by asterisk and triangle respectively. D, immunofluorescence of mock-infected (U) and WSN-infected A549 cells treated with TIZ (5 μg/ml) or vehicle for 24 h, labeled with anti-p230 trans-Golgi (red) and anti-HA (green) antibodies. Nuclei are stained with DAPI (blue). The overlay of the three fluorochromes is shown (merge). The enlarged areas (insets) highlight the localization of HA in untreated and TIZ-treated cells. Images were captured and deconvolved with a DeltaVision microscope using SoftWoRx-2.50 software. Bar=5 μm.

Figure 5:
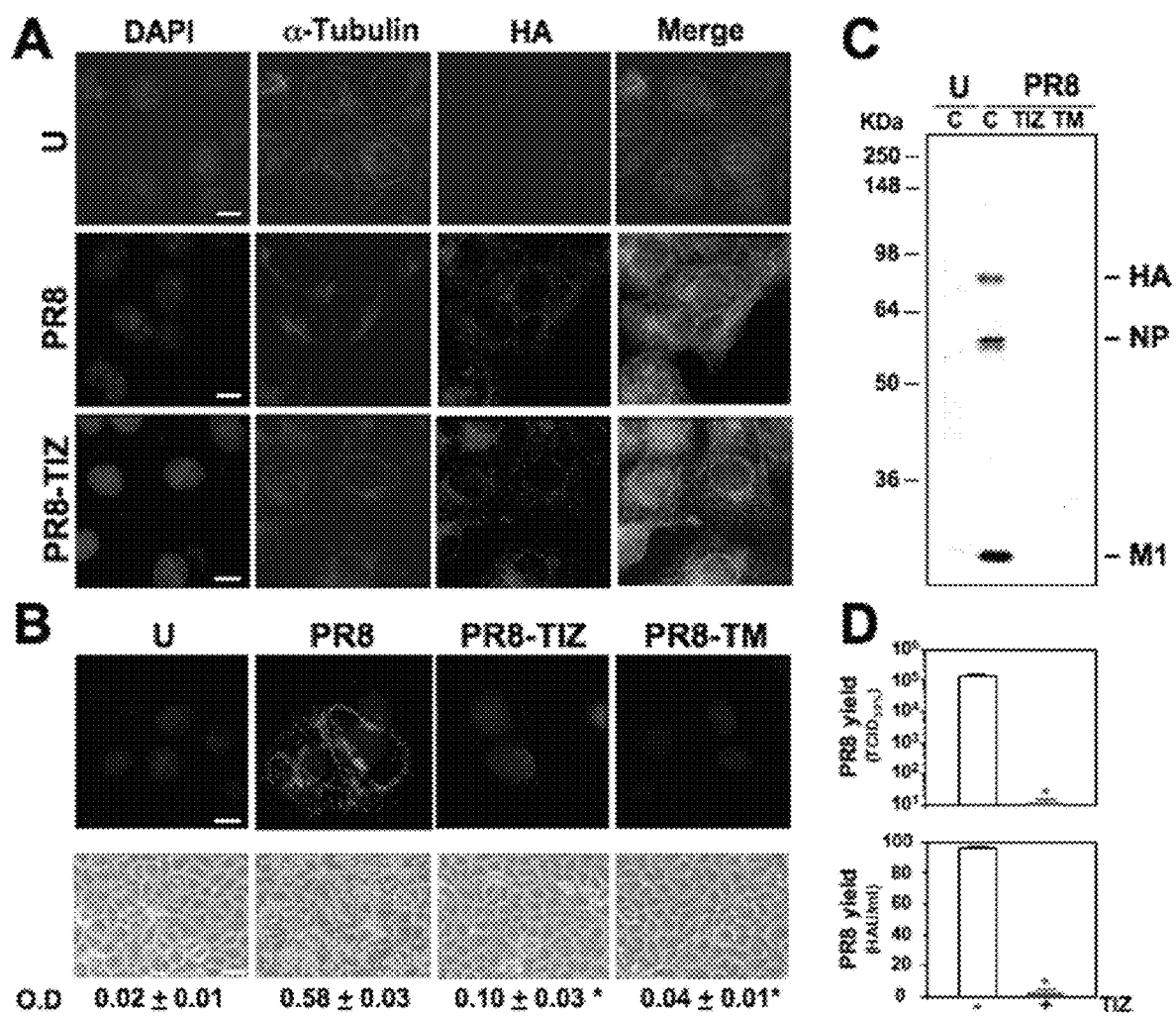
FIG. 5. Tizoxanide inhibits transport of influenza hemagglutinin to the cell surface. A, levels of total hemagglutinin (green) and α-tubulin (red) were detected in mock-infected (U) and untreated or TIZ-treated (10 μg/ml) PR8-infected MDCK cells at 16 h p.i. by indirect immunofluorescence (bar=10 μm). Nuclei are stained with DAPI (blue). The overlay of the three fluorochromes is shown (merge). Images were captured and deconvolved with a DeltaVision microscope using the SoftWoRx-2.50 software. B, levels of plasma-membrane hemagglutinin (green) were detected at 16 h p.i. by indirect immunofluorescence (top) in mock-infected or PR8-infected cells treated with 10 μg/ml TIZ or 5 μg/ml TM. Nuclei are stained with Hoechst 33342 (blue). Images were processed as in A (bar=10 μm). The overlay of the two fluorochromes is shown. Erythrocytes hemadsorption on plasma-membrane at 5 h p.i. is shown in parallel samples (bottom) (bar=35 μm). Hemoglobin levels of bound erythrocytes were quantified spectrofotometrically (λ=540 nm). Data, expressed in optical density (O.D.), represent the mean±SD of duplicate samples from a representative experiment of two with similar results. *=P<0.05 vs. infected-control. C, autoradiography of [35S]-Met/Cys-labeled proteins incorporated into viral particles purified at 24 h p.i. from supernatants of mock-infected or PR8-infected cells treated as in B. Viral proteins (HA, NP, M1) are indicated. D, in parallel, virus yield was determined in untreated (empty bars) or TIZ-treated (filled bars) PR8-infected cells at 24 h p.i. by infectivity assay (top) and hemagglutination assay (bottom). Data, expressed in TCID50/ml and HAU/ml respectively, represent the mean±SD of duplicate samples from a representative experiment of two with similar results. *=P<0.05 vs. infected-control.

FIG. 5. Tizoxanide inhibits transport of influenza hemagglutinin to the cell surface. A, levels of total hemagglutinin (green) and α-tubulin (red) were detected in mock-infected (U) and untreated or TIZ-treated (10 μg/ml) PR8-infected MDCK cells at 16 h p.i. by indirect immunofluorescence (bar=10 μm). Nuclei are stained with DAPI (blue). The overlay of the three fluorochromes is shown (merge). Images were captured and deconvolved with a DeltaVision microscope using the SoftWoRx-2.50 software. B, levels of plasma-membrane hemagglutinin (green) were detected at 16 h p.i. by indirect immunofluorescence (top) in mock-infected or PR8-infected cells treated with 10 μg/ml TIZ or 5 μg/ml TM. Nuclei are stained with Hoechst 33342 (blue). Images were processed as in A (bar=10 μm). The overlay of the two fluorochromes is shown. Erythrocytes hemadsorption on plasma-membrane at 5 h p.i. is shown in parallel samples (bottom) (bar=35 μm). Hemoglobin levels of bound erythrocytes were quantified spectrofotometrically (λ=540 nm). Data, expressed in optical density (O.D.), represent the mean±SD of duplicate samples from a representative experiment of two with similar results. *=P<0.05 vs. infected-control. C, autoradiography of [35S]-Met/Cys-labeled proteins incorporated into viral particles purified at 24 h p.i. from supernatants of mock-infected or PR8-infected cells treated as in B. Viral proteins (HA, NP, M1) are indicated. D, in parallel, virus yield was determined in untreated (empty bars) or TIZ-treated (filled bars) PR8-infected cells at 24 h p.i. by infectivity assay (top) and hemagglutination assay (bottom). Data, expressed in TCID50/ml and HAU/ml respectively, represent the mean±SD of duplicate samples from a representative experiment of two with similar results. *=P<0.05 vs. infected-control.

FIG. 6 Antiviral activity of Zanamivir at three concentrations and Zanamivir combined with Nitazoxanide at 0.1 ug/mL against Influenza A. Zanamivir was tested alone against influenza A (MDCK/PR8) at doses of 0.01, 0.1 and 1.0 μM and in the presence of NTZ at 0.1 μg/ml.

FIG. 7 Antiviral activity of Zanamivir at three concentrations and Zanamivir combined with Nitazoxanide at 1.0 ug/mL against Influenza A. Zanamivir was tested alone against influenza A (MDCK/PR8) at doses of 0.01, 0.1 and 1.0 μM and in the presence of NTZ at 1.0 μg/ml.

FIG. 8 Antiviral activity of Oseltamivir at three concentrations and Oseltamivir combined with Nitazoxanide at 0.1 ug/mL against Influenza A. Oseltamivir was tested alone against influenza A (MDCK/PR8) at doses of 0.01, 0.1 and 1.0 μM and in the presence of NTZ at 0.1 μg/ml.

FIG. 9 Antiviral activity of Oseltamivir at three concentrations and Oseltamivir combined with Nitazoxanide at 1.0 ug/mL against Influenza A. Oseltamivir was tested alone against influenza A (MDCK/PR8) at doses of 0.01, 0.1 and 1.0 μM and in the presence of NTZ at 1.0 μg/ml.

FIG. 10. Antiviral activity of tizoxanide against influenza A and B viruses. A, MDCK cells were infected with four different influenza A virus strains, the mammalian H1N1 PR8 and WSN, and H3N2 A/FI, and the H5N9 avian strain A/Ck at a m.o.i. of 10 HAU/105 cells, and treated with 10 μg/ml TIZ (filled bars) or vehicle (empty bars) immediately after the adsorption period. Virus yield was determined at 24 h p.i. B, long-term antiviral activity of TIZ in MDCK cells infected with influenza B virus (B/Parma/3/04) and treated with 10 μg/ml TIZ (●) or vehicle (M) after virus adsorption. C-D, single-step (C) and multistep (D) PR8 virus growth curves were performed on MDCK cells infected at an m.o.i. of 10 (C) or 0.001 (D) ffu/cell and treated with 10 μg/ml TIZ (●) or vehicle (M) as in A. Virus yield was determined at the indicated times p.i. (A-D) Virus yield, expressed as percent of untreated control (A) or in HAU/ml (B-D) represents the mean±SD of duplicate samples from a representative experiment of three with similar results. *=P<0.01; **=P<0.05.

FIG. 11. Tizoxanide does not influence human low-density lipoprotein receptor (LDLR) plasma membrane targeting. MDCK cells were transiently transfected with green fluorescent protein (GFP)-tagged internalization-defective human low-density lipoprotein receptor mutant (LDLR-A18-GFP plasmid) (40) and, after 8 h, treated with TIZ (10 μg/ml) or vehicle for the following 16 h. After blocking protein synthesis with cycloheximide for 1 h, plasma membranes were stained using CellMask™ Orange plasma membrane (PM) stain, and imaged using a Leica DM-IL fluorescence microscope equipped with UV excitation filters. The images were captured with a Leica DC-300 camera using Leica Image-Manager500 software. Levels of LDLR-GFP (green) and PM (red) were detected in untreated (upper panels) or TIZ treated (bottom panels) transfected MDCK cells. The overlay of the two fluorochromes is shown (merge). Sections of the same images (bar=10 μm) of a representative experiment are shown.

Figure 12:
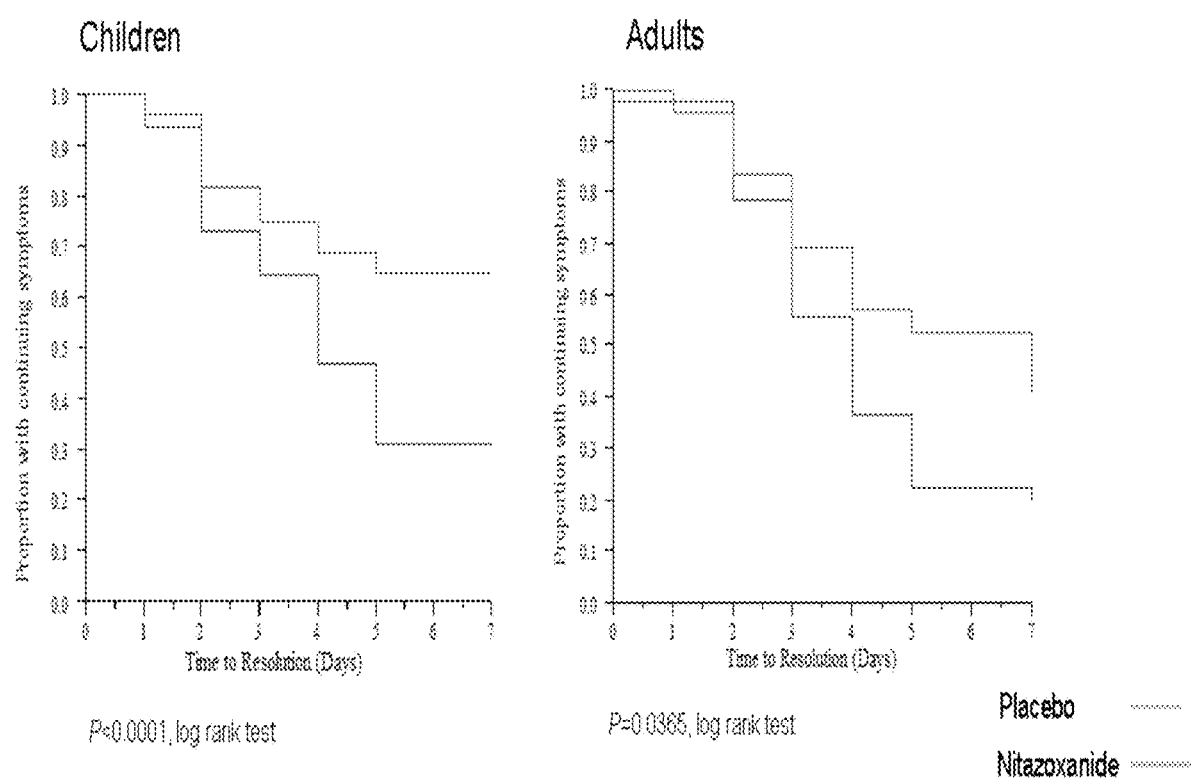
FIG. 12. Results demonstrating that nitazoxanide can resolve symptoms associated with influenza-like illness in subjects who do not test positive for the presence of Adenovirus, RSV, Influenza A, Parainfluenza 1.

FIG. 12. Nitazoxanide can resolve symptoms associated with influenza-like illness.

Figure 13:
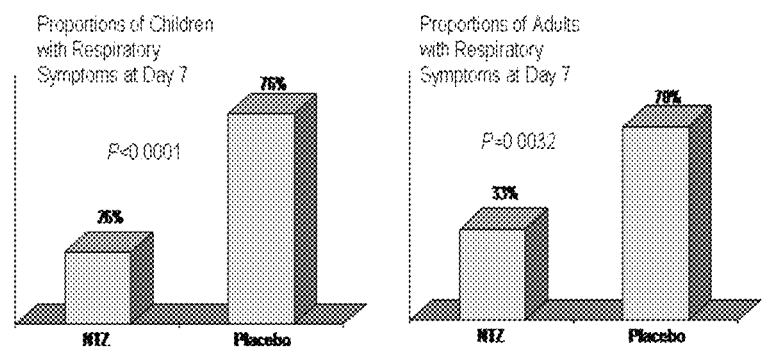
FIG. 13. Day 7 Physical Exam data showing nitazoxanide reduces respiratory symptoms associated with influenza-like illness after.

FIG. 13. Day 7 Physical Exam data—Nitazoxanide reduces respiratory symptoms associated with influenza-like illness after.

Figure 14:
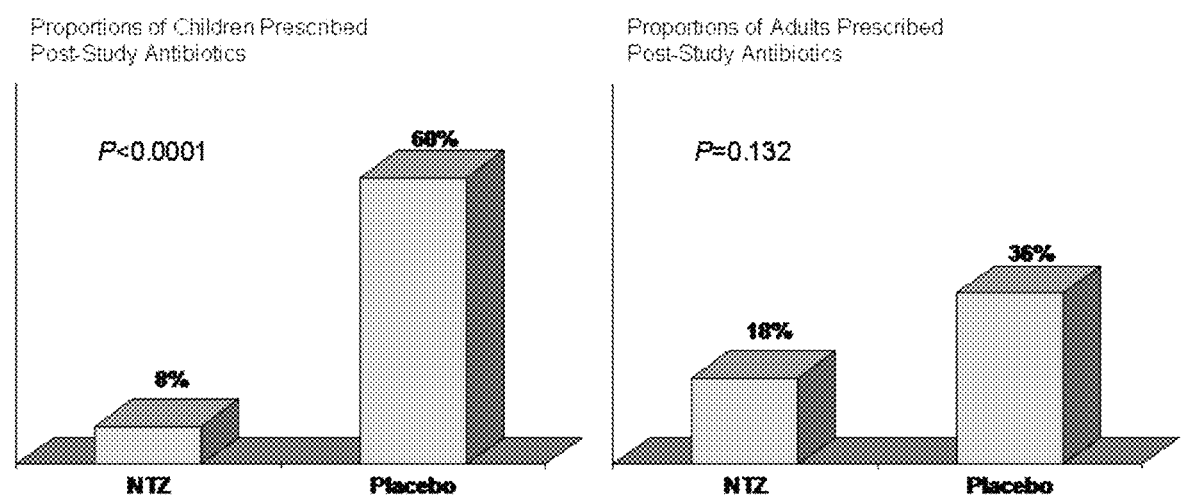
FIG. 14. Post-study antibiotic use in subjects with an influenza-like illness being treated with nitazoxanide or placebo.

FIG. 14. Post-study antibiotic use.

Figure 15:
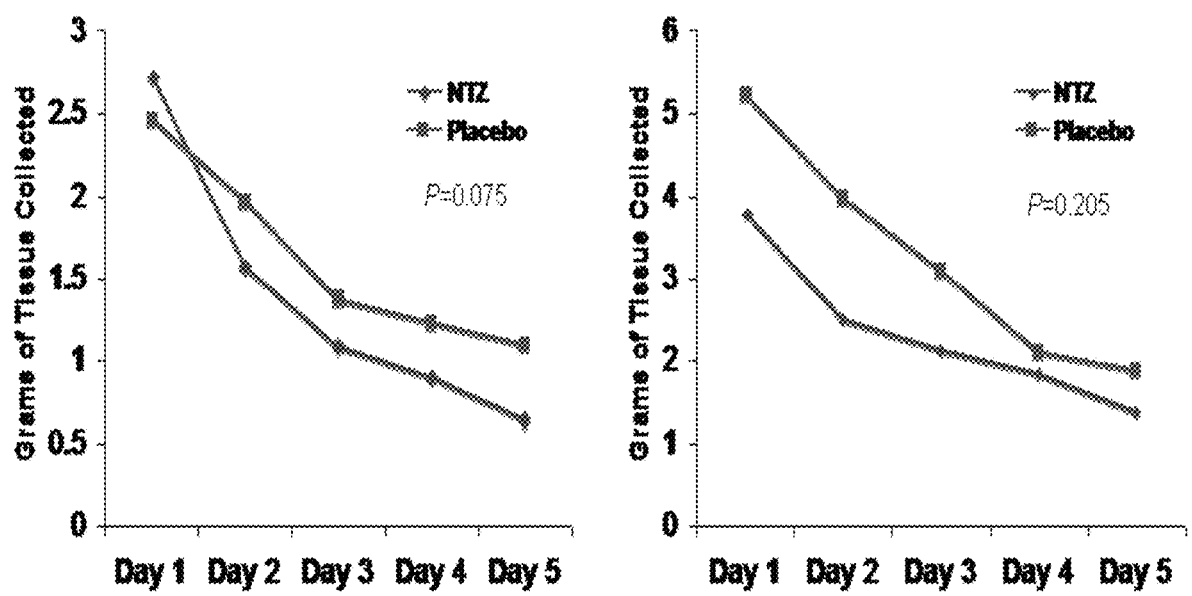
FIG. 15. Weight of Daily Tissue Collection in subjects with an influenza-like illness being treated with nitazoxanide or placebo.

FIG. 15. Weight of Daily Tissue Collection

Compounds (I) of the present invention may be synthesized according to the general scheme below, where R6 and R9 may be selected from nitro (NO2) and SO2R12, by reacting an aroyl derivative, wherein G1 is hydroxy, chloro, fluoro, bromo, alkoxy and the like, with an aminothiazole derivative, as defined herein, under suitable reaction conditions. In some embodiments, the reaction may be generically represented as follows:

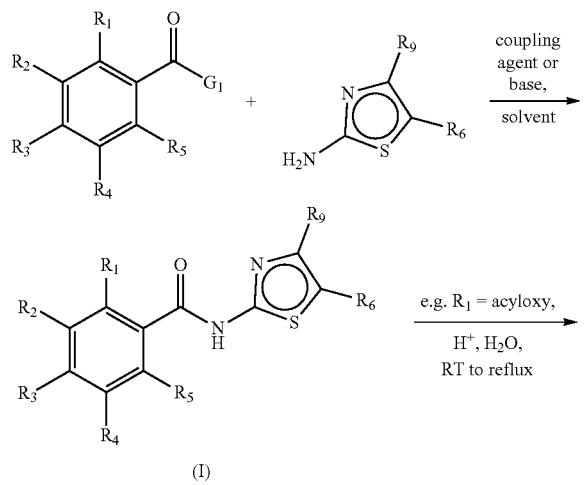

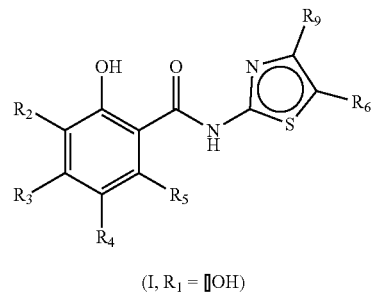

Compounds (I) of the present invention may also be synthesized according to published procedures U.S. Pat. Nos. 3,950,351, 6,020,353, PCT WO2006042195A1 and US2009/0036467A.

Examples of compounds of the present invention may include, but are not limited to the following compounds listed in Table 6. This set of examples is not intended to limit the invention.

TABLE 6

Examples of the Invention

| No. | Compound | m.p. (° C.) |
|---|---|---|
| 1 | | 202 |
| 2 | | 254 |
| 3 | | >300 |
| 4 | | 203-205 |
| 5 | | 259-260 |

TABLE 6-continued

Examples of the Invention

| No. | Compound | m.p. (° C.) |
|---|---|---|
| 6 | 4-acetoxy-benzoyl, N-(5-nitrothiazol-2-yl)amide | 246-248 (dec) |
| 7 | 4-hydroxy-benzoyl, N-(5-nitrothiazol-2-yl)amide | 263-265 |
| 8 | 2-methoxy-benzoyl, N-(5-nitrothiazol-2-yl)amide | 230-232 (dec) |
| 9 | 2-hydroxy-3-methyl-benzoyl, N-(5-nitrothiazol-2-yl)amide | 208-210 |
| 10 | 2-hydroxy-4-methyl-benzoyl, N-(5-nitrothiazol-2-yl)amide | 246-248 (dec) |
| 11 | 2-acetoxy-5-methyl-benzoyl, N-(5-nitrothiazol-2-yl)amide | 187.5-189.5 |
| 12 | 2-hydroxy-5-methyl-benzoyl, N-(5-nitrothiazol-2-yl)amide | 237.5-238.0 |
| 13 | 2-hydroxy-3-methoxy-benzoyl, N-(5-nitrothiazol-2-yl)amide | not determined |

TABLE 6-continued

Examples of the Invention

| No. | Compound | m.p. (° C.) |
|---|---|---|
| 14 | (isobutyl carbonate of 2-hydroxy-N-(5-nitrothiazol-2-yl)benzamide) | 125.3-132.3 |
| 15 | (ethyl carbonate of 2-hydroxy-N-(5-nitrothiazol-2-yl)benzamide) | 159.4-161.4 |
| 16 | (propanoate ester of 2-hydroxy-N-(5-nitrothiazol-2-yl)benzamide) | 158.5-160.5 |
| 17 | (benzoate ester of 2-hydroxy-N-(5-nitrothiazol-2-yl)benzamide) | 229.4-230.4 |
| 18 | (benzoate ester of 2-hydroxy-N-(5-nitrothiazol-2-yl)benzamide) | 180.3-182.3 |
| 19 | (cinnamate ester of 2-hydroxy-N-(5-nitrothiazol-2-yl)benzamide) | 166.2-167.0 |

TABLE 6-continued

Examples of the Invention

| No. | Compound | m.p. (° C.) |
|---|---|---|
| 20 | •HCl SALT (piperidine-4-carboxylate ester of 2-hydroxy-N-(5-nitrothiazol-2-yl)benzamide) | 230 (dec) |
| 21 | •HCl SALT (piperazine-1-carboxylate ester of 2-hydroxy-N-(5-nitrothiazol-2-yl)benzamide) | 244-245 |
| 22 | •HCl SALT (methyl(2-(methylamino)ethyl)carbamate ester of 2-hydroxy-N-(5-nitrothiazol-2-yl)benzamide) | 138.5-140 |
| 23 | acetate ester of 5-fluoro-2-hydroxy-N-(5-nitrothiazol-2-yl)benzamide | 168-172 (dec) |
| 24 | 5-fluoro-2-hydroxy-N-(5-nitrothiazol-2-yl)benzamide | 233-235 (dec) |
| 25 | acetate ester of 5-chloro-2-hydroxy-N-(5-nitrothiazol-2-yl)benzamide | 177-180 |

TABLE 6-continued

Examples of the Invention

| No. | Compound | m.p. (° C.) |
|-----|----------|-------------|
| 26 | 5-chloro-2-hydroxy-N-(5-nitrothiazol-2-yl)benzamide | 236-240 (dec) |
| 27 | 2-(methylsulfonyl-thiazol-2-ylcarbamoyl)phenyl acetate | 175.6-178.8 |
| 28 | 2-hydroxy-N-(4-(methylsulfonyl)thiazol-2-yl)benzamide | 231-235 |
| 29 | 2-(4-(methylsulfinyl)thiazol-2-ylcarbamoyl)phenyl acetate | 167.3-169.3 |
| 30 | 2-hydroxy-N-(4-(methylsulfinyl)thiazol-2-yl)benzamide | 260-261 |
| 31 | 3-(4-(methylsulfonyl)thiazol-2-ylcarbamoyl)phenyl acetate | 209.0-212.0 |

TABLE 6-continued

Examples of the Invention

| No. | Compound | m.p. (° C.) |
|---|---|---|
| 32 | 3-hydroxy-N-(4-(methylsulfonyl)thiazol-2-yl)benzamide | 258.0-259.0 (dec) |
| 33 | 4-(4-(methylthio)thiazol-2-ylcarbamoyl)phenyl acetate | 185.7-188.7 |
| 34 | 4-(4-(methylsulfonyl)thiazol-2-ylcarbamoyl)phenyl acetate | 242.0-246.0 (dec) |
| 35 | 4-hydroxy-N-(4-(methylsulfonyl)thiazol-2-yl)benzamide | 253.0-255.0 (dec) |
| 36 | 2-(4-(isopropylsulfonyl)thiazol-2-ylcarbamoyl)phenyl acetate | 141-145 |

TABLE 6-continued

Examples of the Invention

| No. | Compound | m.p. (° C.) |
|-----|----------|-------------|
| 37  | (2-hydroxyphenyl)-C(O)-NH-thiazole-SO2-iPr | 201-203 ( |
| 38  | (2-acetoxyphenyl)-C(O)-NH-thiazole-SO2-cyclohexyl | 152-155 |
| 39  | (2-hydroxyphenyl)-C(O)-NH-thiazole-SO2-cyclohexyl | 247-250 |
| 40  | (2-acetoxyphenyl)-C(O)-NH-thiazole-SO2-Et | 181.0-186.5 |
| 41  | (2-hydroxyphenyl)-C(O)-NH-thiazole-SO2-Et | 234.7-240.0 |

TABLE 6-continued

Examples of the Invention

| No. | Compound | m.p. (° C.) |
|---|---|---|
| 42 | | 158.7-160.8 |
| 43 | | 192.197 |
| 44 | | 235-238 |
| 45 | | 190-192 |
| 46 | | 216-221 (dec) |

TABLE 6-continued

| | Examples of the Invention | |
|---|---|---|
| No. | Compound | m.p. (° C.) |
| 47 | [structure] | 211-215 |
| 48 | [structure] | 231-232 (dec) |
| 49 | [structure] | 166.9-169.0 |
| 50 | [structure] | 229-230 |

TABLE 6-continued

Examples of the Invention

| No. | Compound | m.p. (° C.) |
|---|---|---|
| 51 | 2-OAc-C6H4-C(O)NH-thiazole-5-SO2-C6H4-4-NO2 | not determined |
| 52 | 2-OAc-C6H4-C(O)NH-thiazole-5-SO2-CH3 | 173-175 |
| 53 | 2-OH-C6H4-C(O)NH-thiazole-5-SO2-CH3 | 282-283 |
| 54 | 2-ONa-C6H4-C(O)NH-thiazole-5-SO2-CH3 | not determined |
| 55 | 2-OAc-C6H4-C(O)NH-thiazole-5-SCH3 | 145-147 |
| 56 | 2-OH-C6H4-C(O)NH-thiazole-5-SCH3 | 225-226 |
| 57 | 2-OAc-C6H4-C(O)NH-thiazole-5-S(CH2)3CH3 | 100-101 |
| 58 | 2-OH-C6H4-C(O)NH-thiazole-5-S(CH2)3CH3 | 180-181 |

TABLE 6-continued

Examples of the Invention

| No. | Compound | m.p. (° C.) |
|---|---|---|
| 59 | 2-OAc-C6H4-C(O)NH-thiazole-5-SO2(CH2)3CH3 | 138-140 |
| 60 | 2-OH-C6H4-C(O)NH-thiazole-5-SO(CH2)3CH3 | 235-236 |
| 61 | 3-OAc-C6H4-C(O)NH-thiazole-5-SMe | 135.2-136.2 |
| 62 | 4-OAc-C6H4-C(O)NH-thiazole-5-SMe | 193.5-195.5 |
| 63 | 4-OAc-C6H4-C(O)NH-thiazole-5-SO2Me | 279.6-280.6 |
| 64 | 4-OH-C6H4-C(O)NH-thiazole-5-SO2Me | 252.5-255.5 |
| 65 | 3-OAc-C6H4-C(O)NH-thiazole-5-SO2Me | 186.5 (dec) |
| 66 | 3-OH-C6H4-C(O)NH-thiazole-5-SO2Me | 271.1-272.3 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

The invention claimed is:

1. A combination comprising a) a therapeutically effective amount of a thiazolide compound, which is nitazoxanide, tizoxanide or a pharmaceutically acceptable salt thereof and b) a vaccine.

2. The combination of claim 1 for treatment a viral infection.

3. The combination of claim 2, wherein the viral infection is an influenza infection.

4. The combination of claim 3, wherein the influenza infection is influenza A infection.

5. The combination of claim 4, wherein the infection is caused by a virus selected from H1N1, H2N2, H3N2, H5N1, H7N7, H1N2, H9N2, H7N2, H7N3, and H10N7.

6. The combination of claim 1, wherein the thiazolide compound is nitazoxanide or a pharmaceutically acceptable salt thereof.

7. The combination of claim 6 for treatment a viral infection.

8. The combination of claim 7, wherein the viral infection is an influenza infection.

9. The combination of claim 8, wherein the influenza infection is influenza A infection.

10. The combination of claim 9, wherein the infection is caused by a virus selected from H1N1, H2N2, H3N2, H5N1, H7N7, H1N2, H9N2, H7N2, H7N3, and H10N7.

* * * * *